United States Patent
Raines

(10) Patent No.: US 11,421,243 B2
(45) Date of Patent: Aug. 23, 2022

(54) ENHANCING PHOTOSYNTHESIS

(71) Applicant: University of Essex Enterprises Limited, Colchester (GB)

(72) Inventor: Christine Raines, Colchester (GB)

(73) Assignee: UNIVERSITY OF ESSEX ENTERPRISES LIMITED

( * ) Notice: Subject to any disclaimer, the term of this patent is extended or adjusted under 35 U.S.C. 154(b) by 504 days.

(21) Appl. No.: 16/079,978

(22) PCT Filed: Feb. 24, 2017

(86) PCT No.: PCT/GB2017/050490
§ 371 (c)(1),
(2) Date: Aug. 24, 2018

(87) PCT Pub. No.: WO2017/144901
PCT Pub. Date: Aug. 31, 2017

(65) Prior Publication Data
US 2019/0062774 A1 Feb. 28, 2019

(30) Foreign Application Priority Data
Feb. 25, 2016 (GB) .................. 1603320

(51) Int. Cl.
*C12N 15/82* (2006.01)
*C07K 14/415* (2006.01)

(52) U.S. Cl.
CPC ........ *C12N 15/8269* (2013.01); *C07K 14/415* (2013.01)

(58) Field of Classification Search
CPC ................................................ C12N 15/8269
See application file for complete search history.

(56) References Cited

U.S. PATENT DOCUMENTS 6,310,271 B1 * 10/2001 Hanson ................ C12N 9/0006
435/410

FOREIGN PATENT DOCUMENTS

| BR | 102012006552 A2 | 8/2015 |
| WO | WO 2002/012273 A2 | 2/2002 |
| WO | WO 2003/020905 A2 | 3/2003 |

OTHER PUBLICATIONS

Wataru, Y. et al., Plant Cell and Environment; Nov. 3, 2015, vol. 39, No. 1; pp. 80-87. (Year: 2015).*
Yamori, W. et al. (publ. online Nov. 3, 2015) Plant Cell and Environment, vol. 39, No. 1; pp. 80-87. (Year: 2015).*
Gupta, R. et al. PNAS (Nov. 26, 2002) vol. 99, No. 24; p. 15806-15811. (Year: 2002).*
Schottler, M.A. et al., Frontiers in Plant Science (May 2014) vol. 5, No. 188; pp. 1-15 (Year: 2014).*
Search Report for GB Patent Application No. 1603320.1, dated Oct. 27, 2016, 3 pages.
Bonfil, D., et al. 1998. A putative HCO3-transporter in the cyanobacterium *Synechococcus* sp. strain PCC 7942. FEBS Letters, 430, pp. 236-240.
Haehnel, W. 1984. Photosynthetic Electron Transport in Higher Plants. Ann.Rev.Plant Physiol, 35, pp. 659-693.
Laisk, A., et al. 1989. The state of the photosynthetic apparatus in leaves as analyzed by rapid gas exchange and optical methods: the pH of the chloroplast stroma and activation of enzymes in vivo. Planta, 177, pp. 350-358.
Lieman-Hurwitz, J., et al. 2003. Enhanced photosynthesis and growth of transgenic plants that express ictB, a gene involved in HCO3-accumulation in cyanobacteria. Plant Biotechnology Journal, 1, pp. 43-50.
Miyagawa, Y., et al. 2001. Overexpression of a cyanobacterial fructose-1,6-/sedoheptulose-1,7-bisphosphatase in tobacco enhances photosynthesis and growth. Nature, 19, pp. 965-969.
Pettersson, G. and Ryde-Pettersson, U., 1988. A mathematical model of the Calvin photosynthesis cycle. Eur.J.Biochem, 175, pp. 661-672.
Poolman, M., et al. 2000. Modelling photosynthesis and its control. Journal of Experimental Botany, 51, pp. 319-328.
Raines, C.A. 2006. Transgenic approaches to manipulate the environmental responses of the C3 carbon fixation cycle. Plant, Cell and Environment, 29, pp. 331-339.
Timm, S., et al. 2012. Glycine decarboxylase controls photosynthesis and plant growth. FEBS Letter, 586, pp. 3692-3697.
Uematsu, K., et al. 2012. Increased fructose 1,6-bisphosphate aldolase in plastids enhances growth and photosynthesis of tobacco plants. Journal of Experimental Botany, 63(4), pp. 3001-3009.
Zhu, X., et al. 2007. Optimizing the Distribution of Resources between Enzymes of Carbon Metabolism Can Dramatically Increase Photosynthetic Rate: A Numerical Simulation Using an Evolutionary Algorithm. Plant Physiology, 145, pp. 513-526.
Clough, S.J et al., "Floral dip: a simplified method for *Agrobacterium*; -mediated transformation of *Arabidopsis thaliana*; ", 1998, The Plant Journal, 16(6), pp. 735-743.
Chida, H. et al., "Expression of the Algal Cytochrome c6 Gene in *Arabidopsis* Enhances Photosynthesis and Growth", 2007, Plant Cell Physiol. 48(7), pp. 948-957.
International Search Report and Written Opinion for International Patent Application No. PCT/GB2017/050490 dated May 31, 2017, 16 pages.
Search Report for GR Patent Application No. 1603320.1 dated Oct. 27, 2016, 3 pages.

(Continued)

*Primary Examiner* — Russell Kallis
(74) *Attorney, Agent, or Firm* — Christina A. MacDougall; Morgan, Lewis & Bockius, LLP

(57) ABSTRACT

Certain embodiments of the present invention relate to methods and products for enhancing the rate of photosynthesis in a plant. In addition, certain embodiments relate to transgenic plants and progeny thereof which comprise an exogenous Rieske Iron Sulphur protein.

Figure 2:
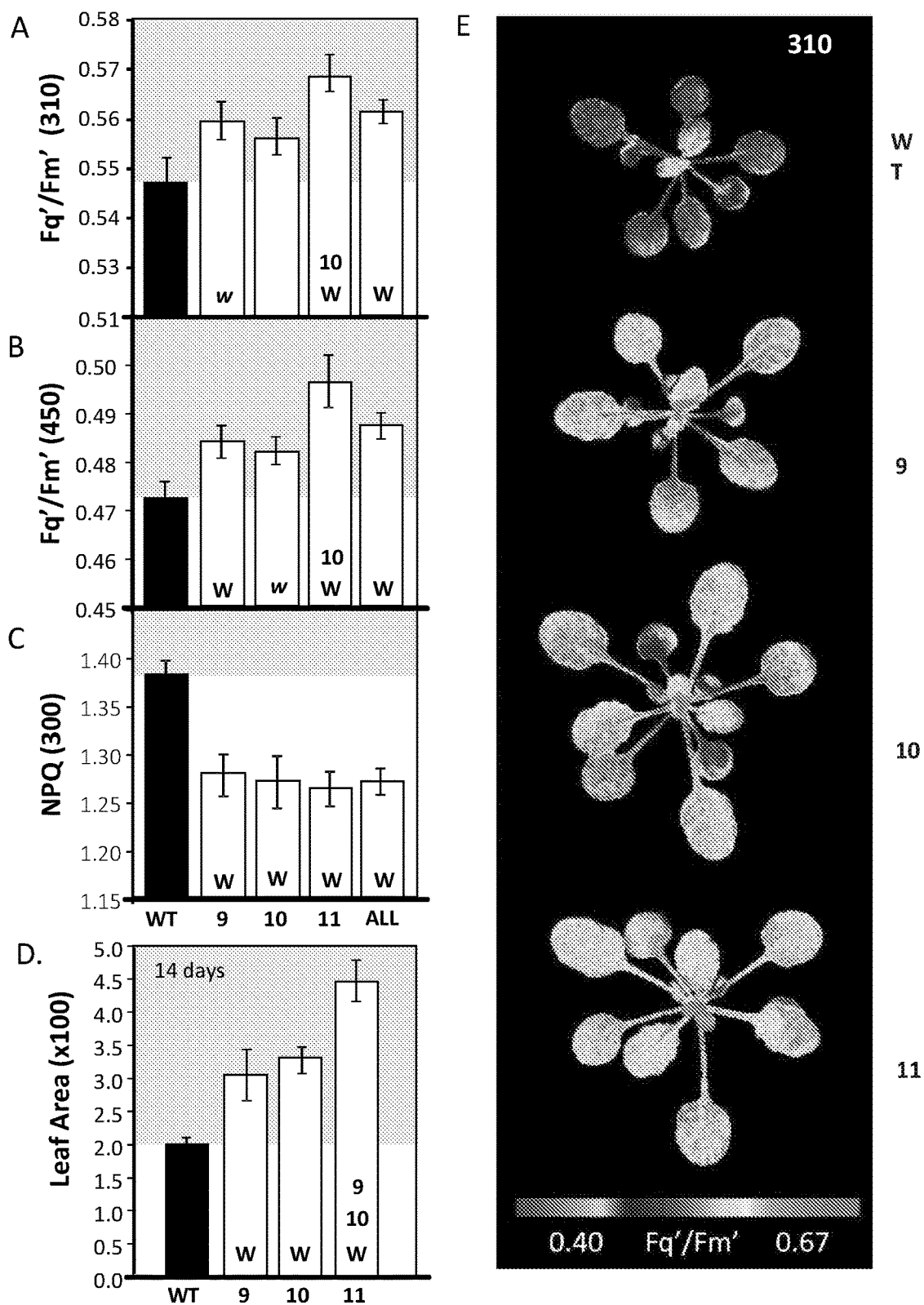

17 Claims, 17 Drawing Sheets
Specification includes a Sequence Listing.

(56) References Cited

OTHER PUBLICATIONS

Palomares et al., Antisense RNA for components associated with the oxygen-evolving complex and the Rieske iron/sulfur protein of the tobacco thylakoid membrane suppresses accumulation of mRNA, but not of protein, Planta, vol. 190, pp. 305-312, 1993.
Yamori et al., "Enhanced leaf photosynthesis as a target to increase grain yield: insights from transgenic rice lines with variable Rieske FeS protein content in the cytochrome b6 /f complex," Plant Cell Environ. vol. 39, No. 1, Nov. 3, 2015.
Yamori et a., "Physiological Functions of Cyclic Electron Transport Around Photosystem I in Sustaining Photosynthesis and Plant Growth," Annual Review of Plant Biology, vol. 67, No. 1, pp. 81-106, Feb. 24, 2016.
Madueno et al., "Import and processing of the precursor of the Rieske FeS protein of tobacco chloroplasts," Plant Mol. Biol., vol. 20, No. 2, pp. 289-299, 1992.
"N. tabacum mRNA for chloroplast Rieske FeS precursor protein 2," Jun. 11, 1992, retrieved from EBI accession No. EM_STD:X66010.
"*Nicotiana tabacum* (common tobacco) Rieske FeS," Jun. 11, 1992, retrieved from EBI accession No. EMBL:CAA46809.
"DNA homologous to phytopathogen resistance-related cDNA— SEQ ID 1619," Jan. 1, 2004, retrieved from EBI accession No. GSN:ADC76350.
"DNA homologous to phytopathogen resistance-related cDNA— SEQ ID 1620," Jan. 1, 2004, retrieved from EBI accession No. GSN:ADC76351.
Knight et al., "Tissue-specific, light-regulated and Plastid-Regulated Expression of the Single-Copy Nuclear Gene Encoding the Chloroplast Rieske FeS Protein of *Arabidopsis thaliana*," Plant and Cell Physiology, vol. 43, Issue 5, May 15, 2002, pp. 522-531.
Richards, "Selectable traits to increase crop photosynthesis and yield of grain crops", Experimental Botany 51,447-458, Feb. 2000.
Zhao et al., "QTLs affecting morph-physiological traits related to drought tolerance detected in overlapping introgression lines of rice (*Oryza sativa* L.)", Plant Science 174, 618-625, Mar. 26, 2008.
Cramer et al., Transmembrane traffic in the cytochrome b6f complex. Annu Rev Biochem 75: 769-790, Jul. 7, 2006.
Baniulis et al., "Structure-function, stability, and chemical modification of the cyanobacterial cytochrome b6f complex from *Nostoc* sp. PCC 7120", J Biol Chern 284: 9861-9869, Dec. 8, 2008.
Schottler et al., Photosynthetic complex stoichiometry dynamics in higher plants: biogenesis, function, and turnover of ATP synthase and the cytochrome b6f complex. J Exp Bot 66: 2373-2400, Dec. 24, 2014.
Anderson J.M., (1992).Cytochrome b6f complex: dynamic molecular organization, function and acclimation. Photosynth.Res. 34, 341-357.
Anderson, J.M., et al., (1997). Reduced levels of cytochrome bf complex in transgenic tobacco leads to marked photochemical reduction of the plastoquinone pool, without significant change in acclimation to irradiance. Photosynth.Res. 53, 215-227.
Hojka et al., "Inducible repression of nuclear-encoded subunits of the cytochrome b6f complex in tobacco reveals an extraordinarily long lifetime of the complex", Plant Physiol 165:1632-1646, 2014.
Schwenkert et al., "Role of the low-molecular-weight subunits PetL, PetG, and PetN in assembly, stability, and dimerization of the cytochrome b6f complex in tobacco", Plant Physiol 144: 1924-1935, Aug. 2007.
Hager et al., "Targeted inactivation of the smallest plastid genome-encoded open reading frame reveals a novel and essential subunit of the cytochrome b(6)f complex", EMBO J 18: 5834-5842, 1999.
Schottler et al., "Knock-out of the plastid-encoded PetL subunit results in reduced stability and accelerated leaf age-dependent loss of the cytochrome b6f complex", Jan. 12, 2007, J Biol Chem 282: 976-985.
Bruce and Malkin, "Biosynthesis of the chloroplast cytochrome b6f complex: studies in a photosynthetic mutant of Lemna", Feb. 1991, Plant Cell 3: 203-212.
Kuras and Wollman, "The assembly of cytochrome b6/f complexes: an approach using genetic transformation of the green alga *Chlamydomonas reinhardtii*", 1994, EMBO J 13: 1019-1027.
Monde et al., "Post-transcriptional defects in tobacco chloroplast mutants lacking the cytochrome b6/f complex", 2000, Plant J 21: 61-72.
Simkin et al., "An investigation of carotenoid biosynthesis in Coffea canephora and Coffea Arabica", Journal of Plant Physiology vol. 165, Issue 10, Jul. 7, 2008, pp. 1087-1106.
Simkin et al., Carotenoid profiling and the expression of carotenoid biosynthetic genes in developing coffee grain. Plant Physiology and Biochemistry vol. 48, Issue 6, Jun. 2010, pp. 434-442.
Baker NR, "Chlorophyll fluorescence: a probe of photosynthesis in vivo", 2008, Annual Review of Plant Biology 59, 89-113.
Baker NR et al., "High resolution imaging of photosynthetic activities of tissues, cells and chloroplasts in leaves", 2001, Journal of Experimental Botany 52: 615-621.
Baker NR, Rosenqvist E, "Applications of chlorophyll fluorescence can improve crop production strategies: an examination of future possibilities", Aug. 2004, Journal of Experimental Botany 55, 1607-1621.
Barbagallo RP et al., "Rapid, non-invasive screening for perturbations of metabolism and plant growth using chlorophyll fluorescence imaging", Jun. 2003, Plant Physiology 132, 485-493.
Bernacchi C.J et al., "Improved temperature response functions for models of Rubisco-limited photosynthesis", 2001, Plant, Cell and Environment 24, 253-260.
Farquhar GD, et al., "A biochemical model of photosynthetic CO2 assimilation in leaves of C3 species", 1980, Planta 149, 78-90.
Fischer RA, Edmeades GO, "Breading and Cereal Yield Progress", 2010, Crop Science Society of America 50, S85-S98.
Harrison EP et al., "Reduced sedoheptulose-1,7-bisphosphatase levels in transgenic tobacco lead to decreased photosynthetic capacity and altered carbohydrate accumulation", 1998, Planta 204 27-36.
Haehnel, W. "Photosynthetic electron transport in higher plants", 1984, Ann.Rev. PlantPhysiol. 35,659-693.
Hope, A.B "Electron transfer amongst cytochrome f, plastocyanin, and photosystem I:kinetics and mechanisms", 2000, Biochim. Biophys. Acta 1456, 5-26.doi: 10.1016/S0005-2728(99)00101-2.
Hu X, et al., "Simple extraction methods that prevent the artifactual conversion of chlorophyll to chlorophyllide during pigment isolation from leaf samples", 2013, Plant Methods. 9: 19.
Inskeep WP, Bloom PR. "Extinction coefficients of chlorophyll a and b in n,ndimethylformamide and 80% acetone", 1985, Plant Physiol 1985, 77:483-48.
Kirchhoff, H. et al., "Control of photosynthetic electron transport by PQ diffusion microdomains in thylakoids of higher plants", 2000, Biochim. Biophys.Acta 1459, 148-168.doi: 10.1016/S0005-2728(00)00143-2.
Lefebvre S et al., "Increased sedoheptulose-1,7-bisphosphatase activity in transgenic tobacco plants stimulates photosynthesis and growth from an early stage in development", May 2005, Plant Physiol 138: 451-460.
Long SP et al.,"Can improvement in photosynthesis increase crop yields?", 2006, Plant, Cell & Environment 29, 315-330.
López-Juez E et al., "New Arabidopsis cue mutants suggest a close connection between plastid- and phytochrome regulation of nuclear gene expression", 1998, Plant Physiol 118, 803-815.
McMurtrie, M.E. et al., "Mathematical models of the photosynthetic response of tree stands to rising CO2 concentrations and temperatures", 1993, Plant, Cell and Environment 16, 1-13.
Murchie EH, Lawson T., "Chlorophyll fluorescence analysis: guide to good practice and understanding some new applications", 2013, Journal of Experimental Botany. 64, 3983-3998.
Nakagawa T et al., "Development of series of gateway binary vectors, pGWBs, for realizing efficient construction of fusion genes for plant transformation", 2007, J. Biosci. Bioeng. 104 (1), 34-41.
Oxborough K, Baker NR. "An instrument capable of imaging chlorophyll a Fluorescence from intact leaves at very low irradiance and at cellular and subcellular levels", 1997, Plant Cell and Environment 20, 1473-1483.

(56) References Cited

OTHER PUBLICATIONS

Parry MAJ et al., "Raising yield potential of wheat. II. Increasing photosynthetic capacity and efficiency", 2011, Journal of Experimental Botany 62, 453-467.

Price, G.D et al., "Chloroplast cytochromeb6/f and ATP synthase complexes in tobacco: transformation with antisense RNA against nuclear-encoded transcripts for the RieskeFeS and ATP polypeptides", 1995, Aust.J.PlantPhysiol. 22, 285-297.doi: 10.1071/PP9950285.

Raines CA. "Increasing photosynthetic carbon assimilation in C3 plants to improve crop yield: current and future strategies", Jan. 2011, Plant Physiology 155, 36-42.

Sharkey TD et al., "Fitting photosynthetic carbon dioxide response curves for C-3 leaves", 2007, Plant, Cell & Environment 30, 1035-1040.

Simkin AJ et al., "Multigene manipulation of photosynthetic carbon assimilation increases CO2 fixation and biomass yield", 2015, Journal of Experimental Botany. 66(13):4075-4090.

Stitt M, et al., "Pathway of starch breakdown in photosynthetic tissues of Pisum sativum", 1978, Biochimica et Biophysica Acta 544, 200-214.

Yamori W et al., "The roles of ATP synthase and the cytochromeb6/f complex in limiting chloroplast electron transport and determining photosynthetic capacity", 2011, Plant Physiology 155, 956-962. doi:10.1104/pp.110.168435.

Zapata M et al., "Separation of chlorophylls and carotenoids from marine phytoplankton, a new HPLC method using a reversed phase C8 col. and phridine-containing mobile phases", 2000, Mar Ecol Prog Ser, 195:29-45.

Zhu XG, et al., "Improving photosynthetic efficiency for greater yield", 2010, Annual Review of Plant Biology 61, 235-226.

Price et al., "Photosynthesis is strongly reduced by antisense suppression of chloroplastic cytochrome bf complex in transgenic tobacco", 1998, Plant Physiol. 25:445-452.

Yamori, "Improving photosynthesis to Increase Food and Fuel Porduction by Biotechnological Strategies in Crops", 2013, J. Plant Biochem. vol. 01, No. 03.

Ermakova et al. (2019) "Overexpression of the Rieske FeS protein of the Cytochrome b 6 f complex increases C 4 photosynthesis in Setaria viridis," Communications biology. 2(1):1-12.

Schmidt et al. (2001) "A comprehensive phylogenetic analysis of Rieske and Rieske-type iron-sulfur proteins," Journal of bioenergetics and biomembranes. 33(1): 9-26.

Schöttler et al. (2015) "Photosynthetic complex stoichiometry dynamics in higher plants: biogenesis, function, and turnover of ATP synthase and the cytochrome b 6 f complex," Journal of experimental botany. 66(9):2373-2400.

GenBank Accession No. P56771.1, "RecName: Full=Cytochrome f; Flags: Precursor", Apr. 7, 2021 [online], 2 pages [retrieved on Jul. 19, 2021] Retrieved from the National Center for Biotechnology Information Database using Internet <URL: https://www.ncbi.nlm.nih.gov/protein/6685374>.

GenBank Accession No. P56773.1, "RecName: Full=Cytochrome b6", Apr. 7, 2021 [online], 2 pages [retrieved on Jul. 19, 2021] Retrieved from the National Center for Biotechnology Information Database using Internet <URL: https://www.ncbi.nlm.nih.gov/protein/6685349>.

GenBank Accession No. X64353.1, "N.tabacum mRNA for Rieske Fe/S protein of cytochrome b6/f complex", Apr. 18, 2005 [online], 2 pages [retrieved on Jul. 19, 2021] Retrieved from the National Center for Biotechnology Information Database using Internet <URL: https://www.ncbi.nlm.nih.gov/nuccore/X64353.1/>.

Stitt et al. (1989) "Metabolite levels in Specific Cells and Subcellular Compartments of Plant Leaves," Methods in Enzymology, vol. 174, pp. 518-552.

\* cited by examiner

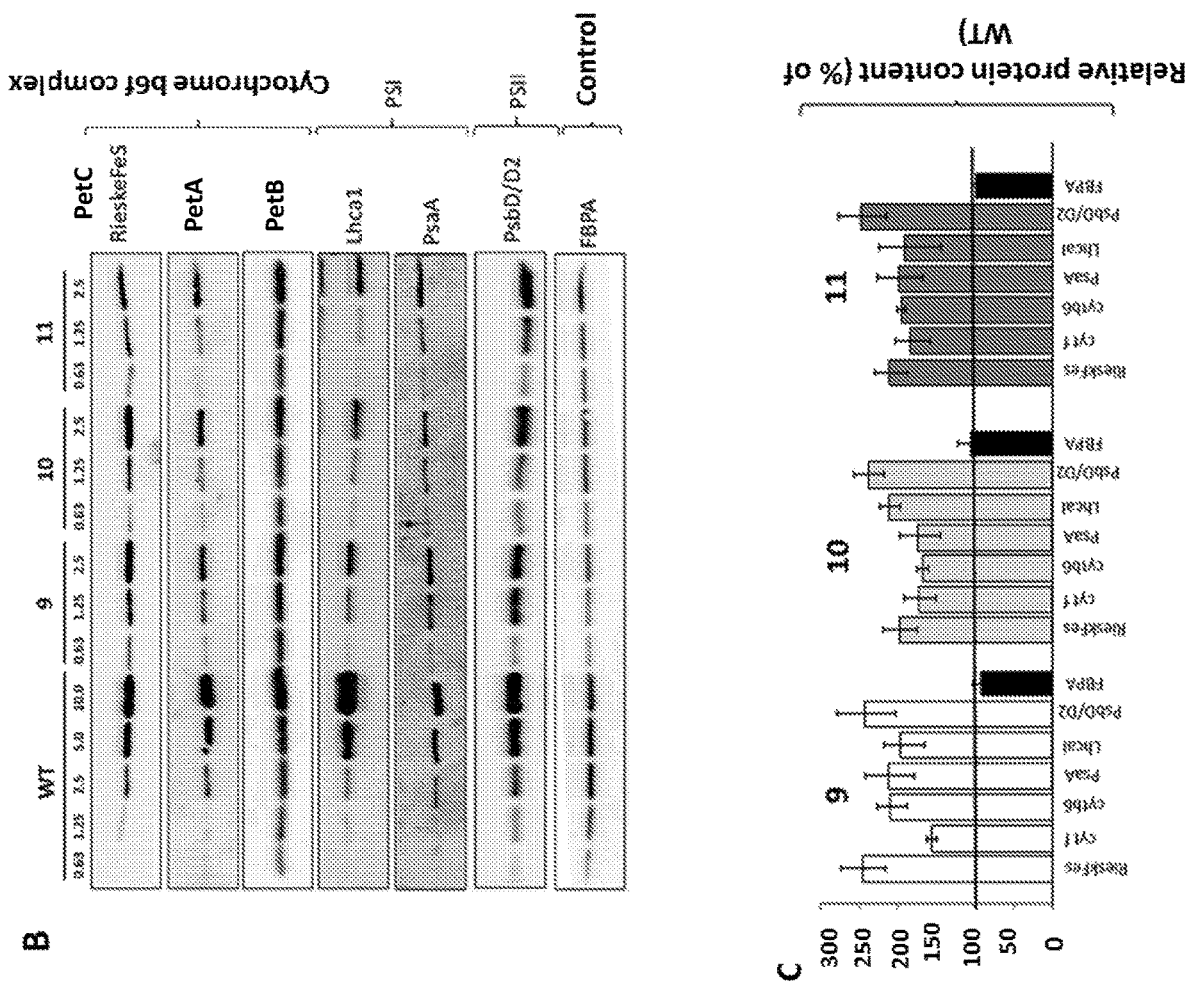
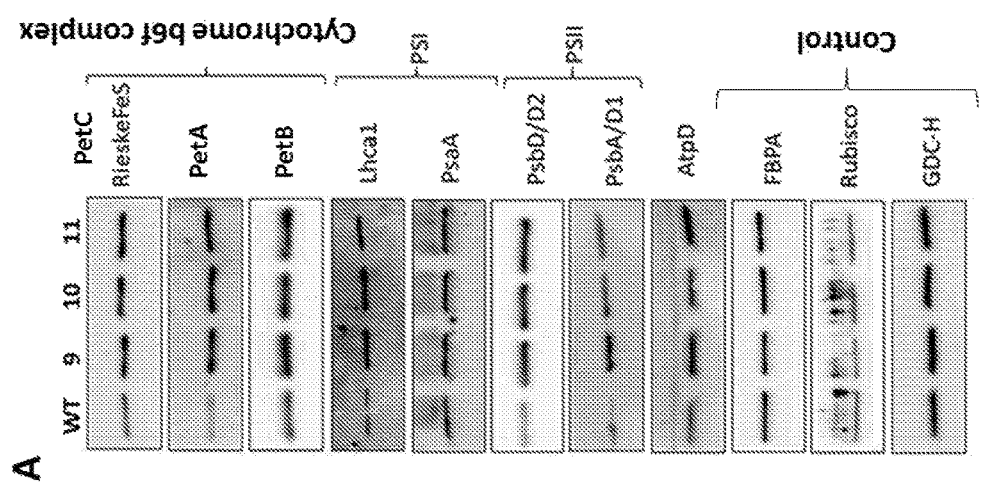
Figure 1

MASSTLSPVTQLCSSKSGLSSVSQCLLLKPMKINSHGLGK
DKRMKVKCMATSIPADDRVPDMEKRNLMNLLLLGALSLPT
AGMLVPYATFFAPPGSGGGSGGTPAKDALGNDVIASEWLK
THPPGNRTLTQGLKGDPTYLVVENDGTLATYGINAVCTHL
GCVVPFNAAENKFICPCHGSQYNNQGRVVRGPAPLSLALA
HADIDDGKVVFVPWVETDFRTGEDPWWA

Figure 12

```
                GCTTCTTCTACTCTTTCTCCAGTAACTCAGCTATGCTC
GAGCAAGAGTGGTTTGTCTTCAGTTTCACAATGTTTGCTAC
TGAAGCCAATGAAGATTAACAGTCATGGATTGGGAAAGGAT
AAGAGGATGAAAGTCAAGTGCATGGCTACAAGCATTCCAGC
AGATGATAGAGTGCCTGATATGGAAAGAGGAATCTCATGA
ATTTGCTTCTTTTGGGTGCTCTTTCTCTACCCACTGCTGGG
ATGTTGGTACCTTATGCTACTTTCTTTGCACCACCTGGGTC
AGGGGGTGGTAGTGGTGGAACCCCTGCCAAGGATGCATTAG
GTAATGATGTCATTGCATCTGAATGGCTCAAAACTCATCCA
CCCGGCAACCGAACTCTCACGCAAGGACTAAAGGGAGATCC
TACTTACCTTGTTGTGGAGAATGATGGAACACTTGCAACCT
ATGGTATTAATGCTGTGTGTACTCACCTTGGTTGTGTTGTG
CCATTTAATGCTGCTGAGAACAAGTTTATTTGCCCCTGCCA
TGGATCTCAATATAACAACCAAGGAAGAGTTGTTAGAGGAC
CTGCTCCTTTGTCCTTGGCATTGGCTCATGCTGACATTGAT
GATGGAAGGTGGTGTTTGTCCCATGGGTTGAAACAGACTT
CAGAACTGGT
```

Figure 13

```
  1 aaatggcttc ttctactctt tctccagtaa ctcagctatg ctcaagcaag agtggcttgt
 61 cttcagtttc acaatgtttg ctagtgaagc caatgaagat taacagtcat ggattgggaa
121 aagataagag gatgaaagtg aaatgcatgg ctacaagtat tccagcagat gatagagtgc
181 ctgatatgga aaagaggaat ctcatgaatt tgcttctttt gggtgctctt tctctaccca
241 ctgctgggat gttggtatct tatggtactt tctttgtacc acctgggtca ggggtggta
301 gtggtggaac ccctgccaag gatgcattag gtaatgatgt cattgcatct gaatggctca
361 aaactcatcc acctggcaac cgaactctca cgcaaggact aaagggagac cctacttacc
421 ttgttgtgga gaatgatgga acagttgcaa cctatggtat taatgctgtg tgtactcacc
481 ttggttgtgt tgtgccattt aatgctgctg agaacaagtt tatttgcccc tgccatggat
541 ctcaatacaa caaccaagga agagttgtta gaggacctgc tcccttgtcc ttggcattgg
601 ctcatgctga tattgatgat gggaaggtgg tgtttgtccc atgggttgaa acagacttca
661 gaactggtga agatccatgg tgggcttaga tctccttatc actatattat cctcttgtat
721 ctttgttaca taaagcttat ctcctttta tgaagcaaaa agaaatattc attttgatga
781 tgtaactatt gaaggataac ctttgcagtc ccataatgac attttttgtt taa
```

Figure 14 maximum PSII operating efficiency (Fq'/Fm')

Non photochemical quenching

Maximum Potential operating efficiency of PSII in the light (Fv'/Fm')

ENHANCING PHOTOSYNTHESIS

CROSS REFERENCE TO RELATED APPLICATIONS

This Application is a U.S. National Phase of International Patent Application No. PCT/GB2017/050490, filed Feb. 24, 2017 and published as WO 2017/144901 A1, which claims priority to United Kingdom Patent Application No. GB 1603320.1, filed Feb. 25, 2016, each of which is hereby incorporated by reference.

FIELD OF THE INVENTION

Certain embodiments of the present invention relate to methods and products for enhancing the rate of photosynthesis in a plant. In addition, certain embodiments relate to transgenic plants and progeny thereof which comprise an exogenous Rieske Iron Sulphur protein.

BACKGROUND TO THE INVENTION

Increasing food and fuel demands caused by a growing world population has led to the need to develop higher yielding crop varieties. It has been estimated that by 2050, a 50% increase in the yield of grain crops such as wheat and rice will be required if food supply is to meet increasing demands (Fischer and Edmeades, 2010). A determinant of crop yield is the cumulative rate of photosynthesis over the growing season which is the result of the crop's ability to capture light, the efficiency by which this light is converted to biomass and how much biomass is converted into the usable product e.g. grain in the case of wheat and rice or biomass in the case of Tobacco. However, the maximum potential yield of a crop over the growing season under optimal conditions is influenced by both genetic factors and agronomic practice.

A number of strategies have been proposed for increasing the yield of crops including selective breeding of plants with traits such as kernel number, stomatal conductance, maximum photosynthesis rate, and carbon isotope discrimination in mind. Increasing photosynthetic capacity has been discussed in the art, although it is considered that it is already a well-optimised process and that increasing leaf photosynthesis rate will not necessarily lead to enhanced crop yield (Richards, (2000) Experimental Botany, 51, 447-458; Zhao et al 2008, Plant Science 174, 618-625). In addition, this field has been held back due to the lack of correlation between leaf photosynthesis and yield, coupled with evidence that yield is sink rather than source limited have led to a pervasive view that crop yields cannot be improved by increasing leaf photosynthetic rates (Long et al 2006).

There are numerous potential targets for increasing yield by way of enhancing photosynthetic capacity. For example, C3 plants fix atmospheric $CO_2$ using the Calvin-Benson cycle enzyme ribulose-1,5-bisphosphate carboxylase/oxygenase (Rubisco). One approach includes improving photosynthetic carbon fixation by increasing the activity of Calvin-Benson cycle enzymes (Lefebvre et al., 2005; Raines, 2011; Simkin et al., 2015). One method is to target Rubisco e.g. to genetically engineer a more efficient Rubisco, or to increase the thermotolerance of Rubisco activase.

There are a number of other parallel systems that have yet to be explored which may impact on the efficiency of the two photosystems, PSI and PSII. For example, the cytochrome b6f (cyt b6f) complex of photosynthetic electron transport acts in both linear electron transport (between PSI and PSII for the generation of ATP and NADPH) and cyclic electron transport (generation of a trans-membrane proton gradient for ATP generation) thereby providing ATP and NADPH for photosynthetic carbon fixation. The electron flow through the Cyt b6/f complex is considered to be a key rate-limiting step for RuBP regeneration (Yamori et al., 2011).

The cytochrome b6f complex is a 220 kDa symmetric dimer, with each monomer being composed of eight subunits. Six of the subunits, PetA (cytochrome f: AtCG00540), PetB (cytochrome b6: AtCG00720), PetD (AtCG00730), PetG (AtCG00600), PetL (AtCG00590) and PetN (AtCG00210) are encoded in the chloroplast genome and 2, PetC (RieskeFeS At4G03280) and PetM (At2G26500), are encoded in the nuclear genome (Cramer et al., 2006; Baniulis et al., 2009; Schottler et al., 2015).

Previous studies have indicated that there is correlation between the capacity of electron transport and the content of the cyt b6f complex. Initially, cyt b6f inhibitors (Kirchhoff et al., 2000) and later transgenic anti-sense studies suppressing the accumulation of the RieskeFeS protein (PetC), a key component of the cyt b6f complex (Price et al., 1995, 1998; Anderson et al., 1997; Yamori et al., 2011), both demonstrated a proportional relationship between linear electron flux and carbon assimilation in leaves, establishing a flux control coefficient close to one for the cyt b6f complex (Price et al., 1995; Kirchhoff et al., 2000). In addition, RNAi repression of PetM, one of the subunits of cytochrome b6f, resulted in a similar phenotype to that shown with RNAi repression of Rieske iron sulphur protein (Hojka et al, Plant Physiology, August 2014, Vol. 165, pp. 1632-1646.)

However, there has been no indication that overexpression of the Rieske iron sulphur protein can lead to increase photosynthesis rate and/or enhanced yield.

This may be due, at least in part, to the recognised complexity of the photosynthetic pathways and particularly the complexity of the cytochrome b6f complex itself. For example, the cytochrome b6f complex comprises both nuclear and chloroplast encoded subunits. Furthermore, it is believed that there is strong posttranscriptional control of complex synthesis and assembly in the chloroplast.

It is an aim of certain embodiments of the present invention to at least partially mitigate the problems associated with the prior art.

It is an aim of certain embodiments of the present invention to provide a method for improving yield of a plant.

It is an aim of certain embodiments of the present invention to provide a method and/or products for upregulating a plurality of components in a cytochrome b6f complex in a plant.

SUMMARY OF CERTAIN EMBODIMENTS OF THE INVENTION

In a first aspect of the present invention, there is provided a method of increasing a photosynthesis rate of a plant, the method comprising expressing within said plant an exogenous Rieske iron sulphur protein to form a transgenic plant.

The cytochrome b6f complex and chloroplast ATP synthase form the predominant sites of photosynthetic flux control. It is considered that the inventors have determined for the first time that overexpression of the Rieske iron sulphur protein may be sufficient to achieve the goal of increasing photosynthesis and yield. Previously, it has been considered that overexpression of a single subunit in the cytb6f complex would be insufficient to achieve this goal. In addition, evidence also suggested that the co-regulation of ATP synthase and the cytochrome b6f complex would be essential to optimise the functions of the thylakoid membrane. Furthermore, it is not known which steps of cytochrome b6f complex bio-genesis ultimately control formation of the complex and there is also a belief that it is most likely the level of cytochrome b6 that coordinates synthesis.

In a second aspect of the present invention, there is provided a method of producing a transgenic plant having an increased photosynthesis rate, the method comprising expressing within said plant an exogenous Rieske iron sulphur protein.

In certain embodiments, the transgenic plant has an increased photosynthesis rate as compared to a control plant.

In certain embodiments, the transgenic plant has a greater size, greater biomass and/or faster growth rate as compared to a control plant. In certain embodiments, the control plant is a wild-type plant of the same variety as the transgenic plant.

In certain embodiments, the method further comprises increasing a level of expression of an endogenous cytochrome b6f complex protein.

In certain embodiments, the method further comprises increasing a level of expression of one or more of an endogenous chlorophyll a-b binding protein (Lhca1), endogenous photosystem I subunit PsaA protein, endogenous photosystem II subunit PsbD protein, endogenous photosystem II subunit PsbA protein and/or endogenous ATP synthase subunit beta protein (AtpD).

In certain embodiments, the method further comprises the step of cultivating the transgenic plant under conditions suitable for photosynthesis to occur.

In certain embodiments, the method further comprises the step of determining an increased photosynthesis rate of the transgenic plant.

In certain embodiments, the method comprises a step of nuclear transformation of a plant cell with a nucleic acid molecule encoding a Rieske iron sulphur protein.

In a third aspect of the present invention, there is provided a method of enhancing yield of a plant, the method comprising expressing within said plant an exogenous Rieske iron sulphur protein to form a transgenic plant.

In certain embodiments, the transgenic plant has an enhanced yield as compared to a control plant. In certain embodiments, the control plant is a wild-type plant of the same variety as the transgenic plant.

In certain embodiments, the enhanced yield comprises a greater size, a greater biomass and/or faster growth rate as compared to the control plant.

In certain embodiments, the method comprises a step of nuclear transformation of a plant cell with a nucleic acid molecule encoding a Rieske iron sulphur protein.

In certain embodiments, the method further comprises:
introducing into at least one plant cell an expression vector comprising a nucleic acid molecule encoding the exogenous Rieske iron sulphur protein; and optionally regenerating a transgenic plant from said at least one plant cell.

In certain embodiments, the expression vector is a plasmid suitable for nuclear transformation of the nucleic acid encoding the Rieske iron sulphur protein. In certain embodiments, the expression vector is not a plasmid which directs transformation of the nucleic acid to the plastid.

In certain embodiments, the method comprises nuclear transformation of the at least one plant cell with a nucleic acid molecule encoding the exogenous Rieske iron sulphur protein.

In certain embodiments, the method further comprises increasing a level of expression of an endogenous cytochrome b6f complex protein.

In certain embodiments, the method further comprises the step of cultivating the transgenic plant under conditions suitable for photosynthesis to occur.

In certain embodiments, the method further comprises the step of determining an increased photosynthesis rate of the transgenic plant.

In certain embodiments, the method further comprises:
cultivating the transgenic plant under conditions promoting plant growth and development; and
optionally obtaining a progeny of said transgenic plant.

In certain embodiments, the method further comprises the step of cultivating the progeny of the transgenic plant under conditions suitable for photosynthesis to occur.

In certain embodiments, the method further comprises the step of determining an increased photosynthesis rate of the progeny of the transgenic plant.

In certain embodiments, the step of obtaining a progeny of said transgenic plant comprises selfing the transgenic plant thereby producing a plurality of first generation progeny plants.

In certain embodiments, the method further comprises the step of cultivating the plurality of first generation progeny plants under conditions suitable for photosynthesis to occur.

In certain embodiments, the method further comprises the step of determining an increased photosynthesis rate of the plurality of first generation progeny plants.

In a further aspect of the present invention, there is provided a method of increasing expression of a cytochrome b6f complex protein in at least one plant cell, the method comprising:
introducing into the at least one plant cell a nucleic acid molecule encoding an exogenous Rieske iron sulphur protein; and
expressing said Rieske iron sulphur protein in said plant cell.

In certain embodiments, the method comprises a step of nuclear transformation of the at least one plant cell with a nucleic acid molecule encoding a Rieske iron sulphur protein.

In certain embodiments, the cytochrome b6f complex protein is selected from PetA, PetB and a combination of PetA and PetB.

In certain embodiments, the cytochrome b6f complex protein is an endogenous cytochrome b6f complex protein.

In certain embodiments, the step of introducing into at least one plant cell a nucleic acid molecule encoding an exogenous Rieske iron sulphur protein comprises introducing an expression vector comprising the nucleic acid molecule encoding the exogenous Rieske iron sulphur protein.

In certain embodiments, the method further comprises the step of cultivating the transgenic plant under conditions suitable for photosynthesis to occur.

In certain embodiments, the method further comprises the step of determining an increased photosynthesis rate of the transgenic plant.

In certain embodiments, the method further comprises regenerating a transgenic plant from said at least one plant cell comprising said nucleic acid molecule.

In certain embodiments, the method further comprises selecting a transgenic plant having an increased expression of a cytochrome b6f complex protein relative to a corresponding control plant.

In certain embodiments, the method further comprises selecting a transgenic plant having an increased photosynthesis rate relative to a corresponding control plant.

In certain embodiments, the control plant is a wild-type plant of the same variety as the transgenic plant.

Aptly, the exogenous Rieske iron sulphur protein comprises an amino acid sequence selected from:
a) an amino acid sequence as set forth in SEQ. ID. No. 1.

Aptly, the exogenous Rieske iron sulphur protein is a protein having an amino acid sequence which has at least 70% sequence identity to the amino acid set forth in SEQ. ID. No. 1.

In certain embodiments, the method further comprises introducing into the at least one cell a nucleic acid molecule comprising a nucleic acid sequence selected from:
a) a nucleic acid sequence as set forth in SEQ. ID. No. 2 or SEQ. ID. No. 3;
b) a nucleic acid sequence having at least 70% sequence identity to the nucleic acid sequence as set forth in SEQ. ID. No. 2 or SEQ. ID. No. 3 and which encodes a Rieske iron sulphur protein;
c) a nucleic acid sequence which hybridises to (a) or (b) and which encodes a Rieske iron sulphur protein; and
d) a nucleic acid sequence which differs from (a), (b) or (c) by virtue of the degeneracy of the genetic code and which encodes a Rieske iron sulphur protein.

In certain embodiments, the nucleic acid molecule is an isolated nucleic acid molecule.

Aptly, the expression vector is a plasmid suitable for nuclear transformation of the nucleic acid encoding the Rieske protein. In certain embodiments, the expression vector is not a plasmid which directs transformation of the nucleic acid to a plastid of the at least one cell.

In a yet further aspect of the present invention, there is provided a chimeric construct for increased expression of a cytochrome b6f protein in a plant, the chimeric construct comprising a nucleic acid molecule, which encodes a Rieske iron sulphur protein, operably linked to a promoter which is operable in a plant cell, wherein the nucleic acid molecule comprises a nucleic acid sequence selected from:
i) a nucleic acid sequence as set forth in SEQ. ID. No. 2 or SEQ. ID. No. 3;
ii) a nucleic acid sequence having at least 70% sequence identity to the nucleic acid sequence as set forth in SEQ. ID. No. 2 or SEQ. ID. No. 3 and which encodes a Rieske iron sulphur protein;
iii) a nucleic acid sequence which hybridises to (a) or (b) and which encodes a Rieske iron sulphur protein; and
iv) a nucleic acid sequence which differs from (a), (b) or (c) by virtue of the degeneracy of the genetic code and which encodes a Rieske iron sulphur protein.

In certain embodiments, the chimeric construct is a plasmid suitable for directing nuclear transformation of the nucleic acid encoding the Rieske iron sulphur protein. In certain embodiments, the chimeric construct is not a plasmid which directs transformation of the nucleic acid to the plastid.

In a yet further aspect of the present invention, there is provided a plant cell comprising a nucleic acid molecule comprising a nucleic acid sequence selected from:
a) a nucleic acid sequence as set forth in SEQ. ID. No. 2 or SEQ. ID. No. 3;
b) a nucleic acid sequence having at least 70% sequence identity to the nucleic acid sequence as set forth in SEQ. ID. No. 2 and which encodes a Rieske iron sulphur protein;
c) a nucleic acid sequence which hybridises to (a) or (b) and which encodes a Rieske iron sulphur protein; and
d) a nucleic acid sequence which differs from (a), (b) or (c) by virtue of the degeneracy of the genetic code, wherein the nucleic acid molecule encodes an exogenous Rieske iron sulphur protein.

Aptly, the nucleic acid molecule is comprised in an expression vector. Aptly, the expression vector further comprises a promoter.

In certain embodiments, the promoter is a 35s *tobacco mosaic virus* promoter.

Aptly, the expression vector is a plasmid. Aptly, the nucleic acid molecule is expressed in the nucleus.

In a yet further aspect of the present invention, there is provided a plant which is regenerated from the plant cell described herein. Aptly, the plant is a monocotyledonous plant.

Aptly, the plant is selected from wheat, barley, rice and canola.

In a further aspect of the present invention, there is provided use of a plant cell which comprises a nucleic acid molecule comprising a nucleic acid sequence selected from:
a) a nucleic acid sequence as set forth in SEQ. ID. No. 2 or SEQ. ID. No. 3;
b) a nucleic acid sequence having at least 70% sequence identity to the nucleic acid sequence as set forth in SEQ. ID. No. 2 and which encodes a Rieske iron sulphur protein;
c) a nucleic acid sequence which hybridises to (a) or (b) and which encodes a Rieske iron sulphur protein; and
d) a nucleic acid sequence which differs from (a), (b) or (c) by virtue of the degeneracy of the genetic code, in the generation of a plant that expresses an exogenous Rieske iron sulphur protein.

In certain embodiments, the plant has one or more of the following characteristics:
a) enhanced yield;
b) increased photosynthesis rate; and/or
c) increased expression of a cytochrome bf6 complex protein.

In certain embodiments, the cytochrome bf6 complex protein is an endogenous cytochrome b6f complex protein.

In certain embodiments, the enhanced yield comprises one or more of:
a) greater biomass;
b) greater size; and/or
c) greater growth rate, as compared to a control plant.

In certain embodiments, the control plant is a wild-type plant of the same variety as the plant that expresses the exogenous Rieske iron sulphur protein.

Thus, in certain embodiments of the present invention, there is provided methods and products which have utility in upregulating one or more components of a cytochrome b6f complex in a plant. The cytochrome b6f complex is an eight subunit complex which forms part of the photosynthetic electron transport chain and acts in both linear electron transport (between PSI and PSII for the generation of ATP and NADPH) and cyclic electron transport (generation of a trans-membrane proton gradient for ATP generation) thereby providing ATP and NADPH for photosynthetic carbon fixation.

The cytochrome b6f complex is composed of 8 different subunits, 6 of which, PetA (cytochrome f: AtCG00540), PetB (cytochrome b6: AtCG00720), PetD (AtCG00730), PetG (AtCG00600), PetL (AtCG00590) and PetN (AtCG00210) are encoded in the chloroplast genome and 2, PetC (RieskeFeS At4G03280) and PetM (At2G26500), are encoded in the nuclear genome (Cramer et al., 2006; Baniulis et al., 2009; Schottler et al., 2015).

The complex functions as a dimer with a proposed molecular weight of approx. 220 kDA with each monomer composed of the eight subunits. The transmembrane domain of the reiskeFeS protein (PetC) and the transmembrane helices of cytochrome b6 (PetB) are directly implicated in the monomer-monomer interaction and stability of the complex (Hager et al., 1999; Schwenkert et al., 2007; Hojka et al., 2014), whereas the petD gene product, is believed to function as a scaffold (Cramer et al., 2006). Furthermore, the PetL gene product is thought to only play a role in complex stability (Schottler et al, 2007). In contrast, PetG, PetN and PetM have all been described as being essential for both cytochrome b6f assembly and stability. (Bruce and Malkin, 1991; Kuras and Wollman, 1994; Hager et al., 1999; Monde et al., 2000; Schwenkert et al., 2007; Hojka et al., 2014).

As used herein, the term "Rieske iron sulphur protein" is interchangeable with the term "RieskeFeS protein" and "PetC". The protein is encoded by the petC gene. The term refers to a RieskeFeS protein of any plant species including for example *Nicotiana tabacum*. Thus, certain embodiments of the present invention involve the use of a RieskeFeS protein provided it is an exogenous protein.

The amino acid sequence of a *N. tabacum* RieskeFeS protein is shown in FIG. 12 and is referred to herein as SEQ ID. No. 1. The amino acid sequence can also be found under accession number: X64353.1 http://www.ncbi.nlm.nih.gov/nuccore/X64353

In certain embodiments, the RieskeFeS protein is a protein having an amino acid sequence as depicted in SEQ. ID. No. 1 or a variant thereof. Variants are discussed herein.

The cDNA sequence of *N. tabacum* PetC which encodes the RieskeFeS protein of FIG. 12 is shown in FIG. 13 and referred to herein as SEQ. ID. No. 2. The *N. tabacum* PetC gene sequence is shown in FIG. 14 and referred to herein as SEQ. ID. No. 3. Certain embodiments of the present invention comprise the use of a nucleic acid molecule comprising the nucleic acid sequence of SEQ. ID. No. 2 or No. 3 or variants thereof. Variants are described herein.

Certain embodiments of the present invention comprise the use of a RieskeFeS protein from a plant species other than *N. tabacum*. For example, in certain embodiments, the RieskeFeS protein is from *Arabidopsis thaliana*. Aptly, the RieskeFeS protein is from for example a perennial monocotyledonous or dicotyledonous plant, including by way of example, *Triticum* species (wheat), *Zea mays* (maize), *Hordeum, Oryza sativa* (rice), *Borago officinalis* (borage), *Camelina* (False flax), *Brassica* species such as *B. campestris, B. napus, B. rapa, B, carinata* (mustard, oilseed rape or turnip rape; *Cannabis sativa* (hemp); *Carthamus tinctorius* (safflower); *Cocos nucifera* (coconut); *Crambe abyssinica* (crambe); *Cuphea* species; *Elaeis guinensis* (African oil palm); *Elaeis oleifera* (American oil palm); *Glycine max* (soybean); *Helianthus annuus* (sunflower); *Linum usitatissimum* (linseed or flax); *Oenothera biennis* (evening primrose); *Olea europaea* (olive). Aptly, the RieskeFeS protein is exogenous to the plant species into which it is introduced.

Thus, in certain embodiments of the present invention, the RieskeFeS protein is a homolog to the RieskeFeS protein of FIG. 12. The term "homolog" is a generic term of the art used to indicate a polypeptide or polynucleotide sequence possessing a high degree of sequence relatedness to a subject sequence. Such relatedness may be quantified by determining the degree of identity and/or similarity between the sequences being compared.

As used herein, the term "percent sequence identity" is the percentage of amino acids or polynucleotides that are identical when the two sequences are compared. Homology or sequence identity of two amino acid sequence or of two nucleic acid sequences may be determined by methods known in the art. For example, the sequence identity may be determined using the algorithm of Karlin and Altschul (1990) *Proc. Natl. Acad. Sci., U.S.A* 87: 2264-2268. Such an algorithm is incorporated into the NBLAST and XBLAST programs of Altschul et al. (1990) *J. Mol. Biol.* 215: 403-410. BLAST nucleotide searches are performed with the NBLAST program, score=100, word length 12, to obtain nucleotide sequences homologous to a nucleic acid molecules of certain embodiments of the present invention. BLAST protein sequences are performed with the XBLAST program, score=50, word length=3, to obtain amino acid sequences homologous to a reference polypeptide (e.g. SEQ. ID. No 1). To obtain gapped alignments for comparison purposes, Gapped BLAST is utilised as described in Altshul et al. (1997) *Nucleic Acids Res.* 25: 3389-3402. When utilising BLAST and Gapped BLAST programs, the default parameters are typically used. (See http://www.ncbi.nlm.nih.gov).

In certain embodiments, the RieskeFeS protein comprises an amino acid sequence which is approx. 70% identical or greater to the amino acid sequence of SEQ. ID. No 1. In certain embodiments, the RieskeFeS protein is at least 80% identical to the amino acid sequence of SEQ. ID. No. 1. In certain embodiments, the RieskeFeS protein is at least 90% identical to the amino acid sequence of SEQ. ID. No 1, e.g. 90%, 91%, 92%, 93%, 94%, 95%, 96%, 97%, 98%, 99% or 100% identical to the amino acid sequence depicted in SEQ. ID. No. 1.

In certain embodiments, the RieskeFeS protein is encoded by a gene comprising a nucleotide sequence which is at least 85% identical to the nucleotide sequence depicted in SEQ. ID. No 3. For example, in certain embodiments, the RieskeFeS protein is encoded by a gene which comprises a nucleotide sequence having a sequence identity of at least 70% identical, e.g. 80% identical, e.g. 90% to the nucleotide sequence of SEQ. ID. No. 3 e.g. 90%, 91%, 92%, 93%, 94%, 95%, 96%, 97%, 98%, 99% or 100% identical to the nucleotide sequence depicted in SEQ. ID. No. 3.

Typically, homologous sequences can be confirmed by hybridization, wherein the hybridization takes place under stringent conditions. Using the stringent hybridization (i.e. washing the nucleic acid fragments twice where each wash is at room temperature for 30 minutes with 2× sodium chloride and sodium citrate (SCC buffer; 1.150. mM sodium chloride and 15 mM sodium citrate, pH 7.0) and 0.1% sodium dodecyl sulfate (SDS); followed by washing one time at 50° C. for 30 minutes with 2×SCC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

In certain embodiments, the RieskeFeS protein is a naturally occurring variant of the protein having an amino acid sequence as depicted in SEQ. ID. No. 1. Non-naturally occurring variants that differ from the protein having an amino acid sequence as depicted in SEQ. ID. No. 1 and have the biological function of a RieskeFeS protein are also encompassed by certain embodiments of the present invention.

In certain embodiments, the RieskeFeS protein comprises one or more conservative amino acid substitution changes, i.e. changes of similarly charged or uncharged amino acids. Genetically encoded amino acids are generally divided into four families:

(1) acidic (aspartate, glutamate);
(2) basic (lysine, arginine, histadine);
(3) non-polar (alanine, valine, leucine, isoleucine, proline, phenylalanine, methionine, tryptophan); and
(4) uncharged polar (glycine, asparagine, glutamine, cysteine, serine, threonine, tyrosine).

As each member of a family has a similar physical and chemical properties as the other members of the same family, it is reasonable to expect that an isolated replacement of a leucine with an isoleucine or valine, a threonine with a serine or a similar replacement of an amino acid with a structurally related amino acid will not have a major effect on the binding properties of the resulting molecule.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macro-molecules of the same type. The term "isolated" with respect to a polynucleotide can refer to a nucleic acid molecule devoid, in whole or in part, of sequences normally associated with it in nature; or a sequence, as it exists in nature but having heterologous sequences in associated therewith; or a molecule dissociated from the chromosome. Purity and homogeneity are typically determined using analytical chemistry techniques, for example, polyacrylamide gel electrophoresis or high performance liquid chromatography. In some embodiments, the term "purified" means that the nucleic acid or protein is at least 85% pure, e.g. at least 90% pure, e.g. 95% pure.

In certain embodiments, a gene encoding a RieskeFeS protein may be expressed in vectors suitable for in vivo expression such as for example plant expression systems. Aptly, the vector is a recombinant expression vector. The term "recombinant expression vector" as used herein refers to a plasmid, virus, cosmid, baculovirus, bacterial, yeast or viral vector or other means known in the art that has been manipulated by insertion or incorporation of the PetC gene which encodes the RieskeFeS protein. Recombinant expression vectors e.g. plasmids for use in certain embodiments of the present invention may be commercially available, publically available on an unrestricted basis, or can be constructed from available plasmids by routine application of well-known, published procedures. Such vectors can be transformed into suitable host cells to form transgenic plants or parts thereof. Suitable vectors include for example gateway-cloning-compatible plant destination vectors for expression of proteins in transgenic plants. Aptly, the vector is a plasmid suitable for nuclear transformation of the gene.

In certain embodiments, the vector is a pGWB2 gateway vector.

The vector is aptly adapted for expression in a plant cell and may comprise one or more regulatory elements necessary for expression of the nucleic acid molecule in a plant operatively linked to the nucleic acid molecule encoding a RieskeFeS protein. The term "operatively linked" as used herein refers to a juxtaposition wherein the components so described are in a relationship permitting them to function in their intended manner.

Certain embodiments of the present invention comprise the use of a promoter and/or other control sequences e.g. enhancers, transcription terminators and the like. A promoter may direct transcription of the gene in question. A promoter may be inducible or constitutive.

In certain embodiments of the present invention, the promoter is a 35S *tobacco mosaic virus* promoter.

In certain embodiments, the vector contains the RieskeFeS coding sequence operably linked to a constitutive promoter (e.g. 35s, or *Figwort Mosaic Virus* promoter). In other embodiments, the coding sequence is operably linked to an inducible promoter. In other embodiments, the coding sequence is operably linked to a tissue specific promoter, which is a photosynthetic tissue specific promoter in some embodiments.

In certain embodiments, the vector may further comprise a selectable marker, that is, a gene encoding a protein necessary for the survival or growth of a host cell transformed with the vector. Such a marker gene may be co-introduced into the host cell or may be containing on the cloning vector. Suitable selection genes encode proteins that confer resistance to antibiotics or other toxic substances for example. Many selection genes are known and could be used with the present invention including, but not limited to, neo, which provides kanamycin resistance and can be selected for using kanamycin, G418, paromomycin, etc.; bar, which confers bialaphos or phosphinothricin resistance; a mutant EPSP synthase protein conferring glyphosate resistance; a nitrilase such as bxn from *Klebsiella ozaenae* which confers resistance to bromoxynil; a mutant acetolactate synthase (ALS) which confers resistance to imidazolinone, sulfonylurea or other ALS inhibiting chemicals; a methotrexate resistant DHFR, a dalapon dehalogenase that confers resistance to the herbicide dalapon; or a mutated anthranilate synthase that confers resistance to 5-methyl tryptophan.

In certain embodiments, the vector comprises one or more genes which encode a protein that confers resistance to kanamycin and/or hygromycin.

With respect to a coding sequence, the term "plant-expressible" means that the coding sequence (nucleotide sequence) can be efficiently expressed by plant cells, tissue and/or whole plants. As used herein, a plant-expressible coding sequence has a GC composition consistent with acceptable gene expression in plant cells, a sufficiently low CpG composition so that expression of that coding sequence is not restricted by plant cells, and codon usage that is consistent with that of plant genes.

In certain embodiments, the vector may be introduced into a host cell. A transgenic plant may be regenerated from the host cell. Transgenic plants can be generated using standard plant transformation methods known to those skilled in the art. The method of transformation depends upon the plant to be transformed.

These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993);

and Methods in Plant Molecular Biology—A Laboratory Manual (Maliga, Klessig, Cashmore, Gruissem & Varner, eds., 1994).

*Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species. The vector may be introduced into the host cell using techniques known in the art, for example floral dipping and/or floral (*Arabidopsis*), *Agrobacterium* infection (tobacco, tomato, soya, casava) or particle bombardment (wheat, barley).

By "transformation", it is meant a permanent or transient genetic change induced in a cell following incorporation of exogenous DNA to the cell. Thus, in certain embodiments, the host cell is transformed with exogenous DNA comprising inter alia a sequence which encodes a RieskeFeS protein.

In certain embodiments, the vector used for transformation is a plasmid. A plasmid may be expressed in the nucleus of a plant cell rather than in a plastid of a plant cell, such as a chloroplast, as would occur if a plastid vector is used. Thus in certain embodiments the exogenous Reiske FeS protein is expressed in the nucleus of the plant cell.

As noted above, a transgenic plant may be regenerated from a transformed plant cell. As used herein, a "transgenic plant" is a plant which has been genetically modified to contain and express recombinant DNA sequences, either a regulatory RNA molecules or as proteins. In certain embodiments, the transgenic plant is genetically modified to express a DNA molecule which encodes an exogenous RieskeFeS protein. As used herein, the term "transgenic plant" also encompasses progeny of an initial transgenic plant, wherein the progeny contain and are capable of expressing the RieskeFeS encoding gene sequence. Additionally, seeds and other plant parts are encompassed within the definition of "transgenic plant" as used herein.

Aptly, the transgenic plant overexpresses the RieskeFeS protein. That is to say, in certain embodiments, the transgenic plant which comprises one or more cells which have been transformed and/or comprise an exogenous RieskeFeS protein, has a level of expression of RieskeFeS protein which is greater than a control plant. The control plant is aptly a plant of the same species as the transgenic plant and which does not comprise an exogenous RieskeFeS protein. Aptly, the control plant is a wild-type plant of the same species as the transgenic plant. In certain embodiments, the control plant is a null segregant in which non-integration of the transgene has been determined.

The transgenic plant may express RieskeFeS protein at a level which is at least 105% e.g. 110%, 115%, 120%, 125%, 130%, 135%, 140%, 145%, 150%, 155%, 160%, 165%, 170%, 175%, 180%, 185%, 190%, 195%, 200% or more as compared to a control plant e.g. a wild-type plant.

The inventors have surprisingly discovered that overexpression of the RieskeFeS protein e.g. by way of introduction of an exogenous gene which encodes a ReiskeFeS protein, expression of other components of the plant's endogenous cytochrome b6f complex is upregulated.

Thus, in certain embodiments, the transgenic plant further comprises a level of expression of endogenous PetA and/or PetB which is greater than the level of expression of PetA and/or PetB of a wild type plant which does not comprise an exogenous RieskeFeS protein. Thus, in certain embodiments, the transgenic plant comprises a level of PetA expression which is at least 105% or greater as compared to the level of PetA expression in a control plant e.g. a wild-type plant. In certain embodiments, the transgenic plant expresses PetA at a level which is at least 105% e.g. 110%, 115%, 120%, 125%, 130%, 135%, 140%, 145%, 150%, 155%, 160%, 165%, 170%, 175%, 180%, 185%, 190%, 195%, 200% or more as compared to a control plant e.g. a wild-type plant.

In certain embodiments, the transgenic plant comprises a level of PetB expression which is at least 105% or greater as compared to the level of PetB expression in a control plant e.g. a wild-type plant. Aptly, the transgenic plant expresses PetB at a level which is at least 105% e.g. 110%, 115%, 120%, 125%, 130%, 135%, 140%, 145%, 150%, 155%, 160%, 165%, 170%, 175%, 180%, 185%, 190%, 195%, 200% or more as compared to a control plant e.g. a wild-type plant.

The amino acid sequence of PetA and PetB proteins will vary according to the species of transgenic plant. By way of example, PetA (cytochrome f: AtCG00540), PetB (cytochrome b6: AtCG00720), gene and protein sequences can be found in PetA http://www.ncbi.nlm.nih.gov/protein/6685374 PetB http://www.ncbi.nlm.nih.gov/protein/6685349

It was also discovered that other proteins involved in electron transport such as chlorophyll a-b binding protein (Lhca1), endogenous photosystem I subunit PsaA protein, endogenous photosystem II subunit PsbD protein, endogenous photosystem II subunit PsbA protein and endogenous ATP synthase subunit beta protein (AtpD) may also be upregulated.

Thus, in certain embodiments, the transgenic plant further comprises a level of expression of an endogenous protein selected from chlorophyll a-b binding protein (Lhca1), endogenous photosystem I subunit PsaA protein, endogenous photosystem II subunit PsbD protein, endogenous photosystem II subunit PsbA protein and endogenous ATP synthase subunit beta protein (AtpD) which is greater than the level of expression of such a protein of a wild type plant which does not comprise an exogenous RieskeFeS protein. Thus, in certain embodiments, the transgenic plant comprises a level of one or more of chlorophyll a-b binding protein (Lhca1), endogenous photosystem I subunit PsaA protein, endogenous photosystem II subunit PsbD protein, endogenous photosystem II subunit PsbA protein and endogenous ATP synthase subunit beta protein (AtpD) which is at least 105% or greater as compared to the level of expression in a control plant e.g. a wild-type plant. In certain embodiments, the transgenic plant expresses one or more of such proteins at a level which is at least 105% e.g. 110%, 115%, 120%, 125%, 130%, 135%, 140%, 145%, 150%, 155%, 160%, 165%, 170%, 175%, 180%, 185%, 190%, 195%, 200% or more as compared to a control plant e.g. a wild-type plant.

As used herein, the term "plant" refers to all genera and species of higher and lower plants of the Plant Kingdom. The term includes the mature plants, seeds, shoots ad seedlings, and part, propagation material, plant organ tissue, protoplasts, callus and other cultures, for example cell cultures, derived from them, and all other species of groups of plant cells giving functional or structural units. Mature plants refers to plants at any developmental stage beyond the seedling. Seedling refers to a young, immature plant at an early developmental stage.

Plants of any species are included in embodiments of the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Certain embodiments of the present invention relate to plants such as for example perennial monocotyledonous or dicotyledonous plants, including by way of example, *Triticum* species (wheat), *Zea mays* (maize), *Hordeum*, *Oryza sativa* (rice), *Borago officinalis* (borage), *Camelina* (False flax), *Brassica* species such as *B. campestris, B. napus, B. rapa, B, carinata* (mustard, oilseed rape or turnip rape; *Cannabis sativa* (hemp); *Carthamus tinctorius* (safflower); *Cocos nucifera* (coconut); *Crambe abyssinica* (crambe); *Cuphea* species; *Elaeis guinensis* (African oil palm); *Elaeis oleifera* (American oil palm); *Glycine max* (soybean); *Helianthus annuus* (sunflower); *Linum usitatissimum* (linseed or flax); *Oenothera biennis* (evening primrose); *Olea europaea* (olive).

In certain embodiments, a transgenic plant as described herein will have a greater biomass than a control plant of the same species which is cultivated in similar or identical conditions. In certain embodiments, the transgenic plant comprises a biomass which is at least 20% greater than the biomass of a wild-type plant e.g. 30%, 40%, 50%, 60%, 70%, 80%, 90%, 100%, 110% or greater.

In certain embodiments, the transgenic plant as described herein shows a characteristic of yield which is improved as compared to a control plant. The characteristics may be selected from:
a) greater biomass;
b) greater size; and/or
c) greater growth rate, as compared to a control plant.

Therefore, in certain embodiments of the invention it is shown that the manipulation of the cytochrome b6f complex by way of overexpression of an exogenous RieskeFeS protein has the potential to influence photosynthesis, growth and seed yield.

DETAILED DESCRIPTION OF EMBODIMENTS OF THE INVENTION

Certain embodiments of the present invention will now be described hereinafter, by way of example only, with reference to the following figures:

FIGS. 1A and B is an image of Western blot gels:

Western blot analysis in fully expanded leaves from three expressing lines. Protein extracts from leaf discs taken from two independent leaves per plant. PetA and PetB are subunits of the cytochrome b6f complex. Lhca amd PsaA are PSI proteins and PsbD/D2 and PsbA/D1 are PSII proteins. AtpD is ATP synthase protein. Controls for protein loading including the calvin cycle enzyme FBP aldolase (FBPA), the photorespiration protein glycine decarboxylase H-subunit (GDC-H) and Rubisco small subunit (Rubisco). B) Wild type proteins were loaded in a range from 0.63 µg to 10 µg and then compared to protein fractions loaded from lines 9, 10 and 11.

FIG. 1C) The level of each protein in each plant line was statistically analysed against wild type grown plants and is shown as a relative percentage of wild type levels.

FIG. 2: Determination of photosynthetic capacity and leaf area in transgenic seedlings using fluorescence imaging. WT and transgenic plants were grown in controlled environment conditions with a light intensity of 130 m$^{-2}$ s$^{-1}$, 8 h light/16 h dark cycle for 14 days and fluorescence imaging used to determine $F_q'/F_m'$ (maximum PSII operating efficiency) at two light intensities. Fluorescence $F_q'/F_m'$ images taken at (a) 310 µmol m$^{-2}$ s$^{-1}$ and (b) 450 µmol m$^{-2}$ s$^{-1}$. (c) A significant decrease in non-photochemical quenching (NPQ) was also observed in these plants (d) leaf area at time of analysis and e) is a fluorescence image of the leaves of WT and transgenic plants.

The data was obtained using 4-6 individual plants from each line compared to 6 WT. Significant differences (p<0.05) are represented as capital letters indicating if each specific line is significantly different from another. Lower case italic lettering indicates lines are just below significance (>0.05-<0.1).

Figure 3:
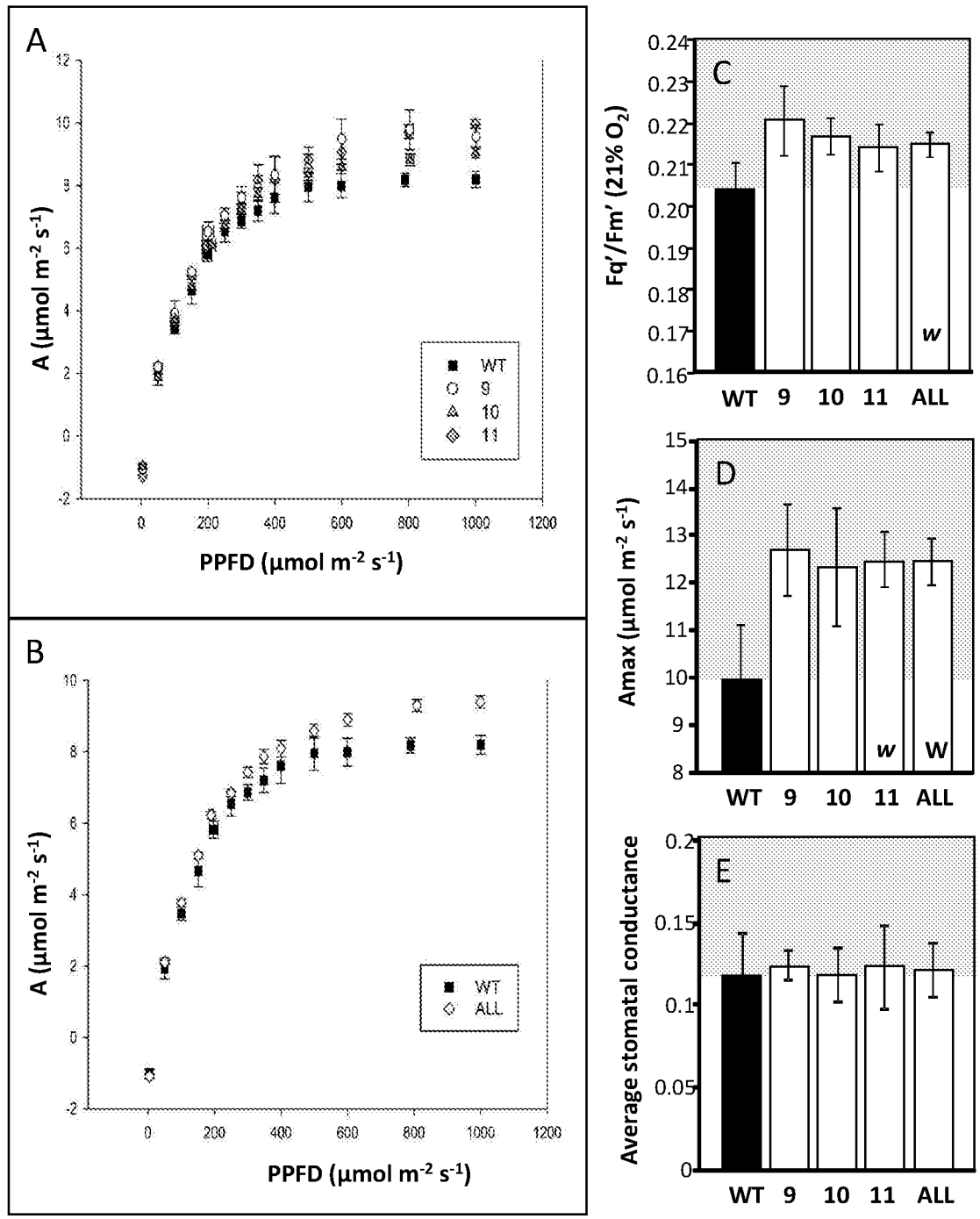

FIG. 3: Determination of photosynthetic capacity in transgenic plants at 21% $O_2$. WT and transgenic plants were grown in controlled environment conditions with a light intensity 130 µmol m$^{-2}$ s$^{-1}$, 8 h light/16 h dark cycle for four weeks and Light Response curves were carried out at 2% $O_2$. (a) is a light Response Curves for each individual rieskeFeS and (b) is a light response curve for all lines combined compared to wild type (WT). (c) is a graph showing average $F_q'/F_m'$ data, (d) is a graph showing Amax, (e) is a graph showing average stomatal conductance over the evaluating period. The data was obtained using 4 individual plants per line compared to 4 WT. (ALL: combined data set of all over-expressing lines). Significant differences (p<0.05) are represented as capital letters indicating if each specific line is significantly different from another.

Figure 4:
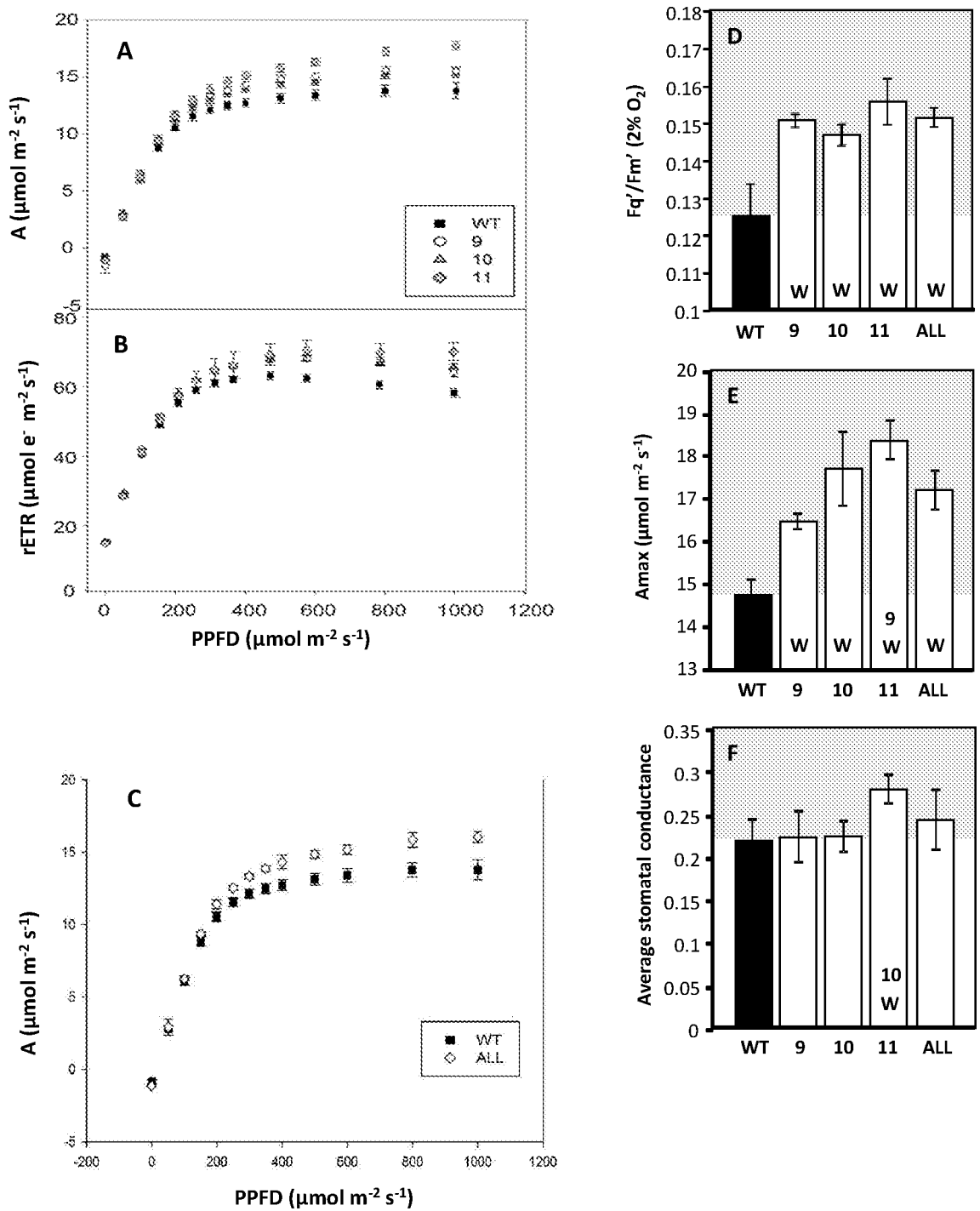

FIG. 4: Determination of photosynthetic capacity and rate of electron transport (rETR) in transgenic plants at 2% $O_2$. WT and transgenic plants were grown in controlled environment conditions with a light intensity 130 µmol m$^{-2}$ s$^{-1}$, 8 h light/16 h dark cycle for four weeks and Light Response curves were carried out at 2% $O_2$. A) is a graph showing light Response Curves for each individual RieskeFeS ox, B) is a graph showing rETR for individual plant lines compared to wild type and C) is a graph showing light response curves for all plant lines combined compared to wild type (WT). D) is a graph showing average $F_q'/F_m'$ data, E) is a graph showing Amax F) is a graph showing average stomatal conductance over the evaluating period. The data was obtained using 4 individual plants per line compared to 4 WT. (ALL: combined data set of all over-expressing lines). Significant differences (p<0.05) are represented as capital letters indicating if each specific line is significantly different from another.

Figure 5:
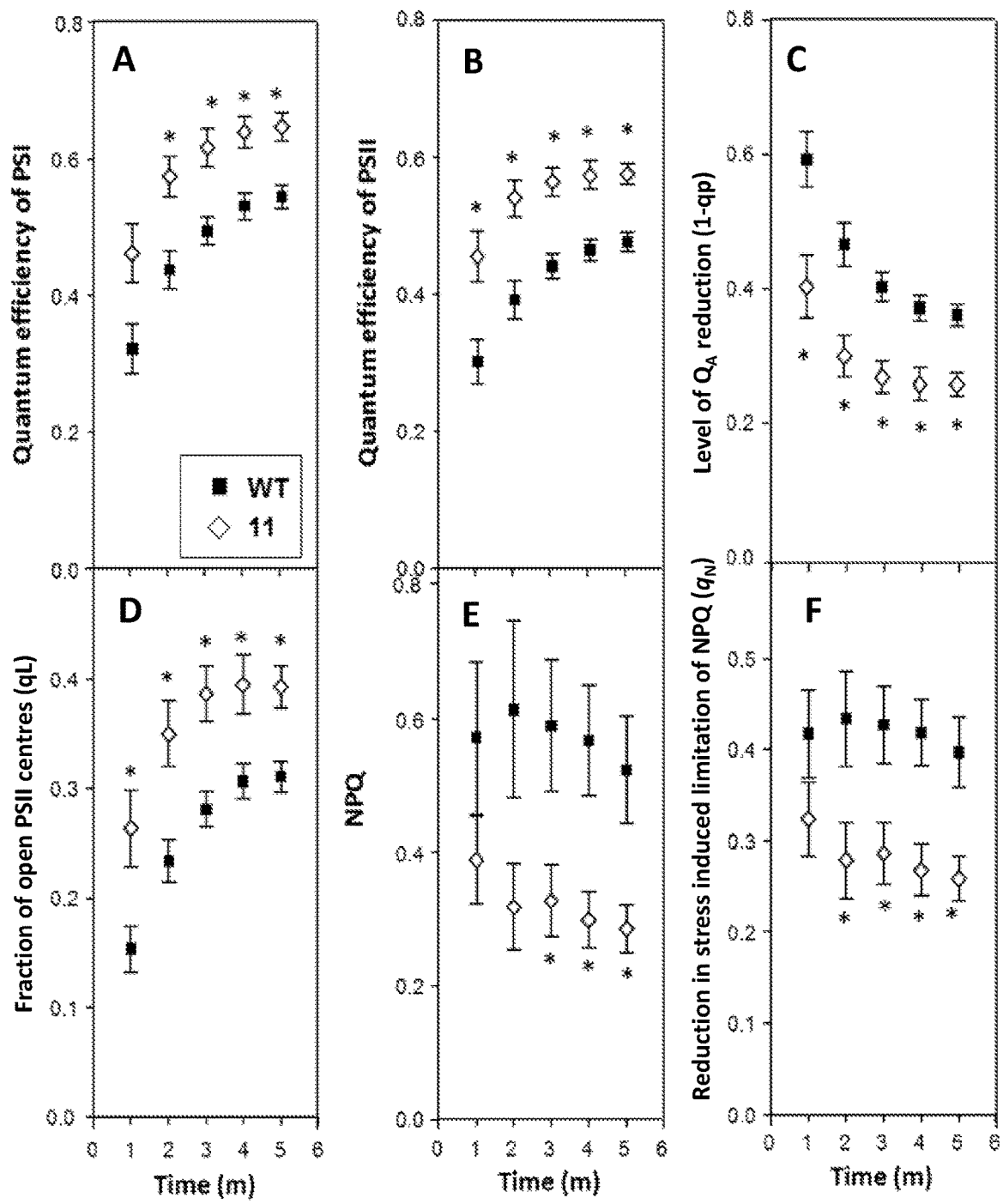

FIG. 5: Determination of the efficiency of electron transport in the leaves of young Rieske Fes ox plants (27 days after planting). WT and Rieske FeS ox plants were grown in controlled environment conditions with a light intensity of 130 mmol m$^{-2}$ s$^{-1}$, 8 h light/16 h dark cycle and the redox state was determined using a Dual-PAM at a light intensity of 220 mmol m$^{-2}$ s$^{-1}$. The data was obtained using four individual plants from Rieske FeS ox line 11 and compared to WT (five plants). Significant differences are indicated (*p<0.05). Bars represent standard errors. The quantum efficiency of PSI (FIG. 5A), quantum efficiency of PSII (FIG. 5B), level of $Q_A$ reduction (1-qp) (5C), fraction of open PSII centres (FIG. 5D), NPQ (FIG. 5E) and reduction in stress induced limitation of NPQ ($q_N$) (FIG. 5F) are all shown.

Figure 6:
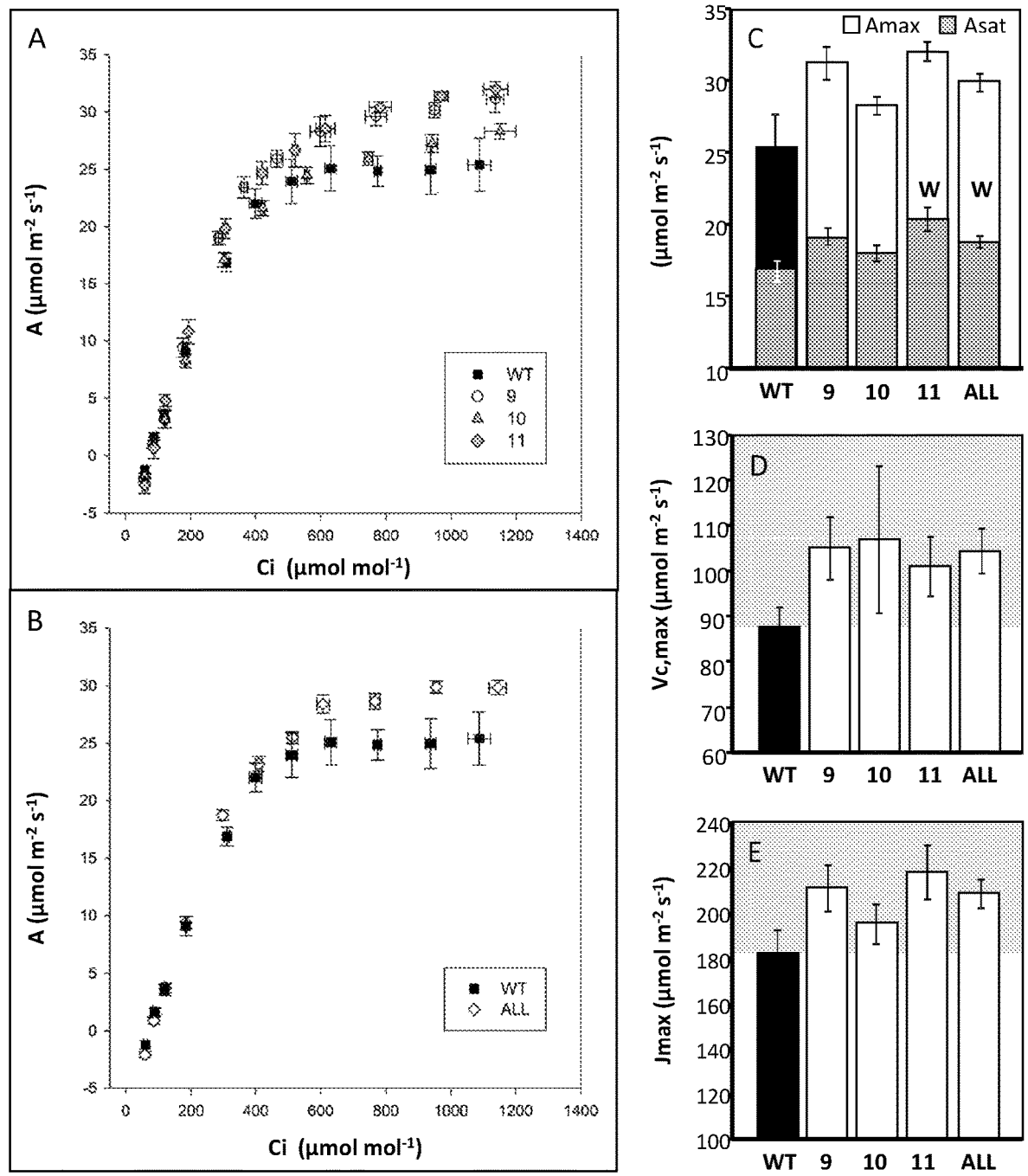

FIG. 6: Photosynthetic responses of WT and transgenic plants grown in greenhouse under square wave isolights. Photosynthetic carbon fixation rates were determined as a function of increasing $CO_2$ concentrations (A/Ci) at saturating-light levels in developing leaves. WT and transgenic plants were grown in controlled environment conditions with a light intensity 280 μmol m$^{-2}$ s$^{-1}$, 12 h light/12 h dark cycle for four weeks. (a) is a graph showing A/Ci Curves for each individual rieskeFeS and (b) is a graph showing all lines combined compared to wild type (WT). (c) $A_{max}/A_{sat}$, (d) is a graph showing Rubisco activity and (e) is a graph showing $J_{max}$ derived from A/Ci response curves using the equations published by von Caemmerer and Farquhar (1981). Significant differences (<0.05) are represented by capital letters. Lower case italic lettering indicates lines are just below significance (>0.05-<0.1).

Figure 7:
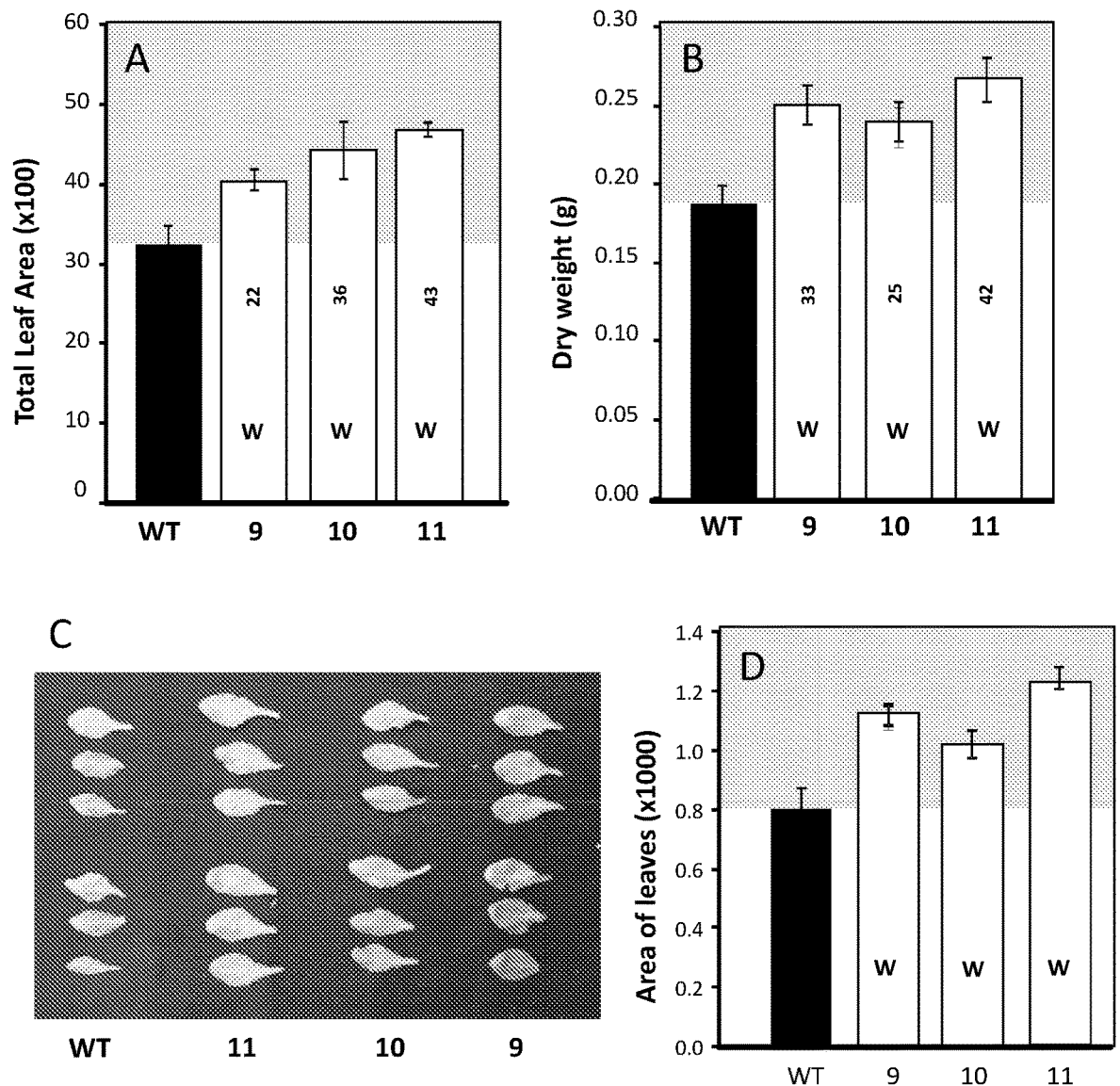

FIG. 7: Final leaf area and biomass of WT and transgenic plants were grown in controlled environment conditions with a light intensity 280 μmol m$^{-2}$ s$^{-1}$, 12 h light/12 h dark cycle for four weeks. (a) Total leaf area (b) dry weight (d) area of leaves of all lines. FIG. 7C is a photograph of the WT and transgenic leaves. Significant differences (p<0.05) are represented by capital letters within the histogram.

Figure 8:
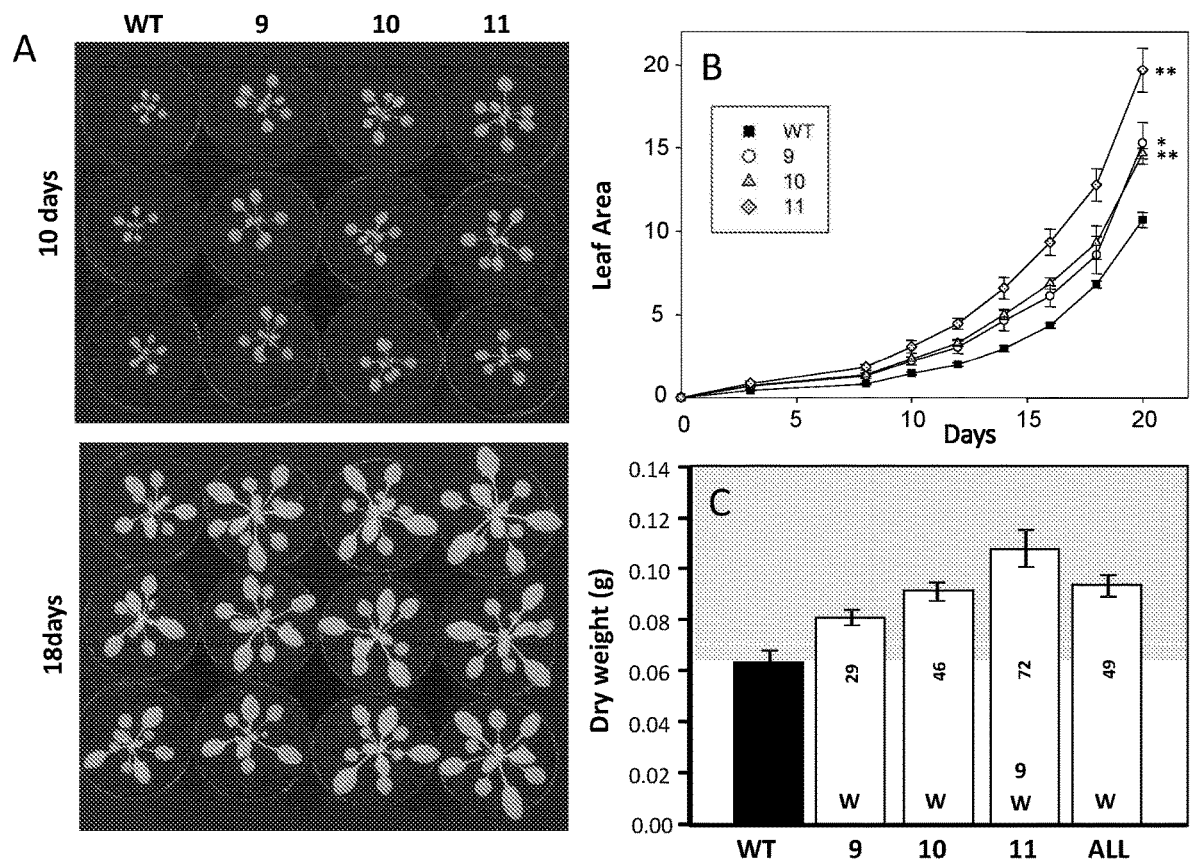

FIG. 8: Growth analysis of wild type (WT) and transgenic lines grown in low light. Plants were grown at 130 μmol m$^{-2}$ s$^{-1}$ light intensity in long days (8 h/16 h days). (a) is a photograph showing the appearance of plants at 10 and 18 days after planting. (b) is a graph illustrating plant growth rate evaluated over the first 20 days. (c) is a graph illustrating final biomass at 25 days post planting. % increase over wild type are indicated as numbers within the histogram. Results are representative of 6 to 9 plants from each line. Significant differences * (p<0.01), ** (p<0.001), are indicated.

Figure 9:

FIG. 9: Schematic representation of the RieskeFeS over-expression vector pGWRi. RB, T-DNA right border; Pnos, nopaline synthase promoter; NTP II, neomycin phosphotransferase gene; Tnos, nopaline synthase terminator; P35S, rbcS2B promoter (1150 bp; At5g38420). Constructs were used to transform wild *Arabidopsis* (Col-0).

Figure 10:
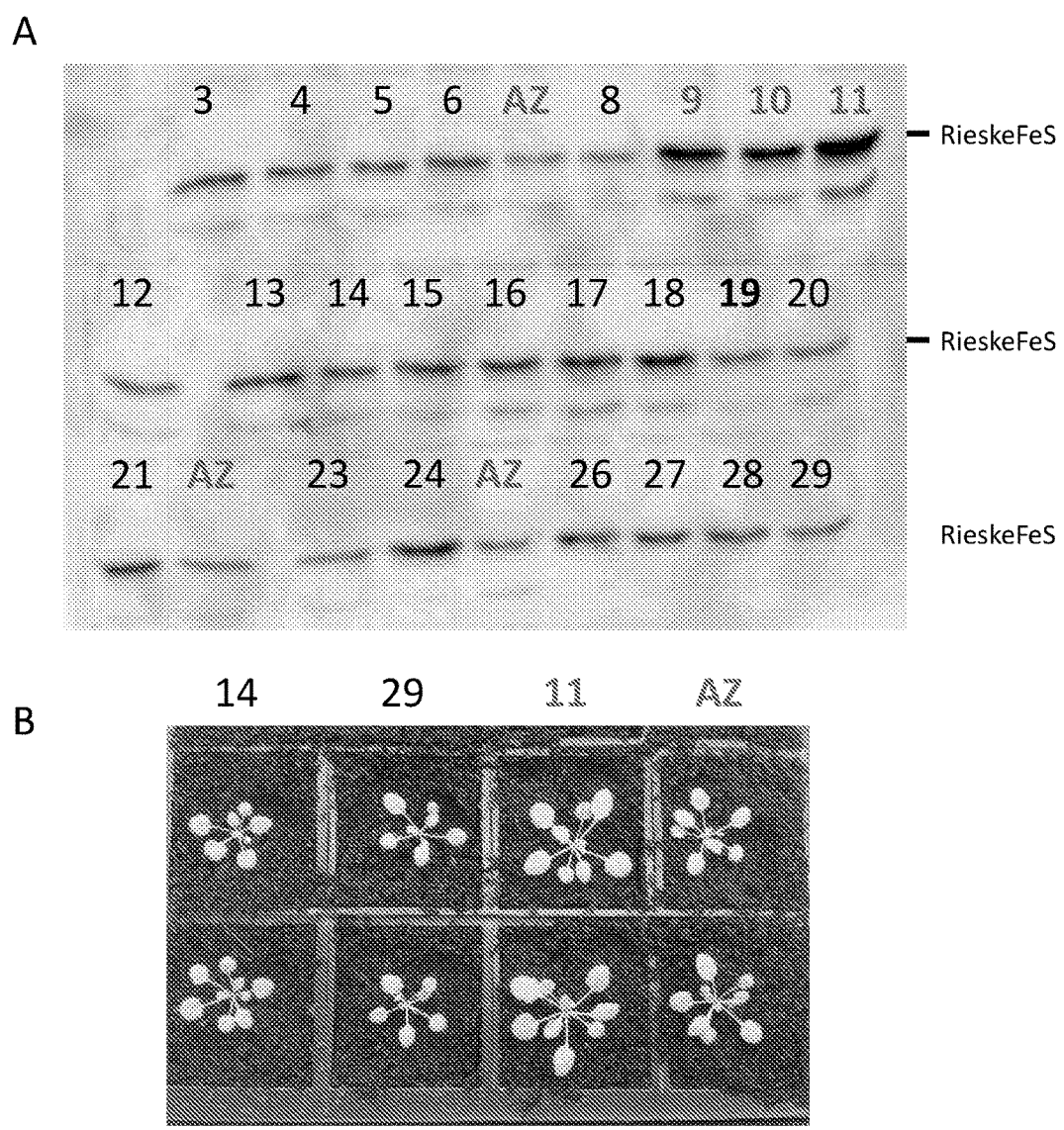

FIG. 10: Molecular and Biochemical Analysis of the transgenic plants over-expressing the RieskeFeS protein from tobacco. Western blot analysis in fully expanded leaves from 27 primary lines. Protein levels were compared to PCR negative lines (AZ). Lines 9, 10 and 11 were selected for study and line 19 was used as a negative control in some studies. FIG. 10B is a photograph of the plant leaves.

Figure 11:
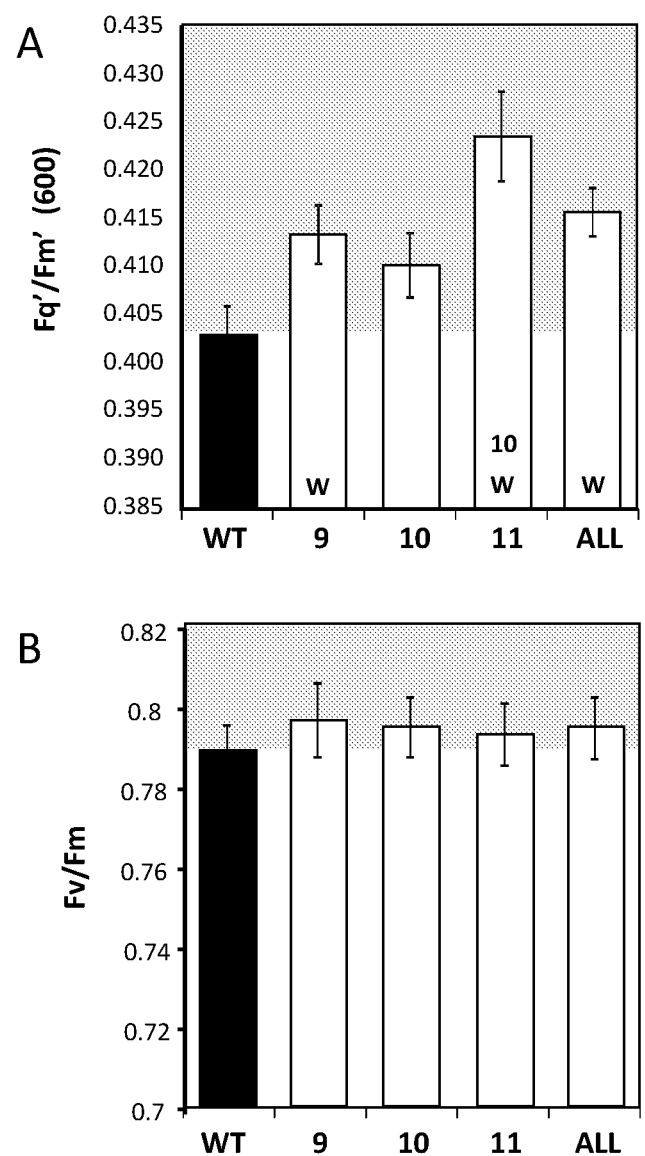

FIG. 11: Determination of photosynthetic capacity and leaf area in transgenic seedlings using fluorescence imaging. WT and transgenic plants were grown in controlled environment conditions with a light intensity of 110 m$^{-2}$ s$^{-1}$, 8 h light/16 h dark cycle for 14 days and fluorescence imaging used to determine $F_q'/F_m'$ (maximum PSII operating efficiency) at a light intensity of (a) 600 μmol m$^{-2}$ s$^{-1}$. (b) Shows Fv/Fm of dark adapted plants. (The data was obtained using 4-6 individual plants from each line compared to 6 WT). Significant differences (p<0.05) are represented as capital letters indicating if each specific line is significantly different from another.

FIG. 12: illustrates the amino acid sequence of *N. tabacum* Rieske iron sulphur protein (SEQ. ID. No. 1).

FIG. 13: illustrates the cDNA sequence of *N. tabacum* petC gene (SEQ. ID. No. 2); and FIG. 14: illustrate the DNA sequence of *N. tabacum* petC gene (SEQ. ID. No. 3).

Figure 15:
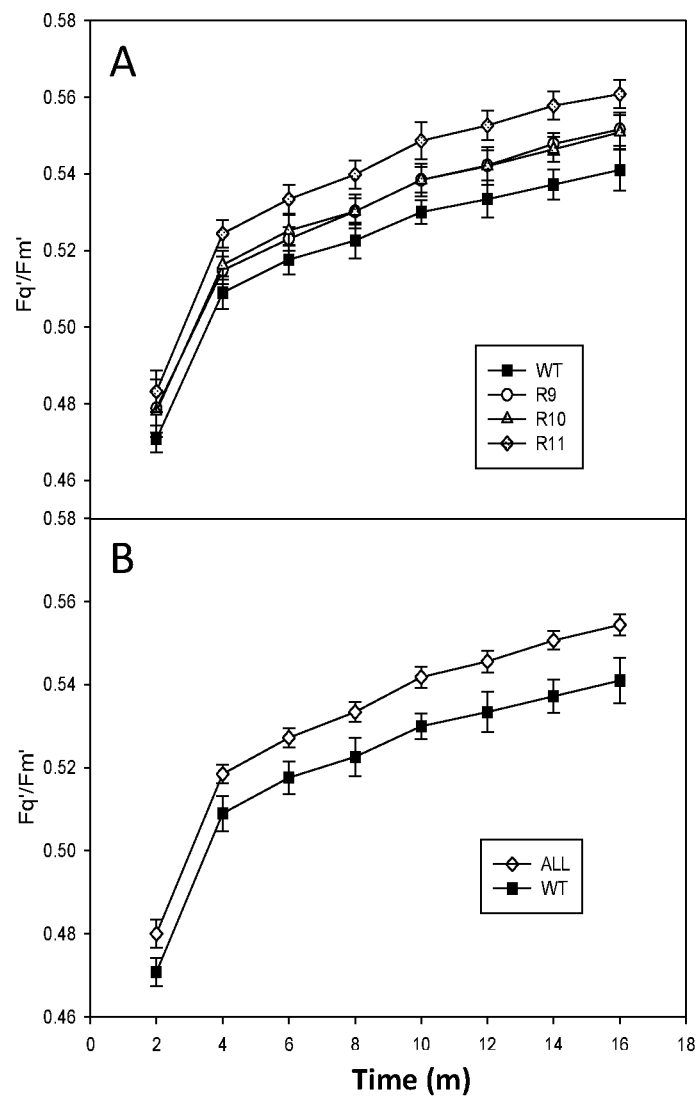

FIG. 15: shows the maximum PSII efficiency ($F_q'/F_m'$). (a) $F_q'/F_m'$ for each individual rieskeFeS and (b) all lines combined compared to wild type (WT).

Figure 16:
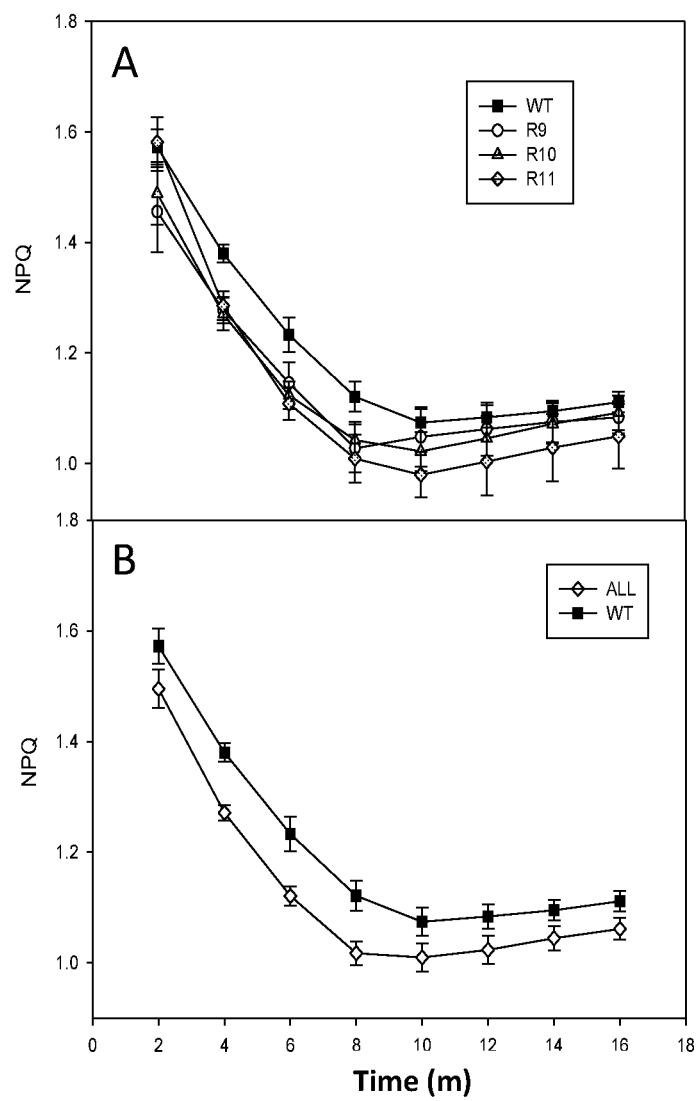

FIG. 16: non-photochemical quenching (NPQ). (a) NPQ for each individual rieskeFeS and (b) all lines combined compared to wild type (WT).

Figure 17:
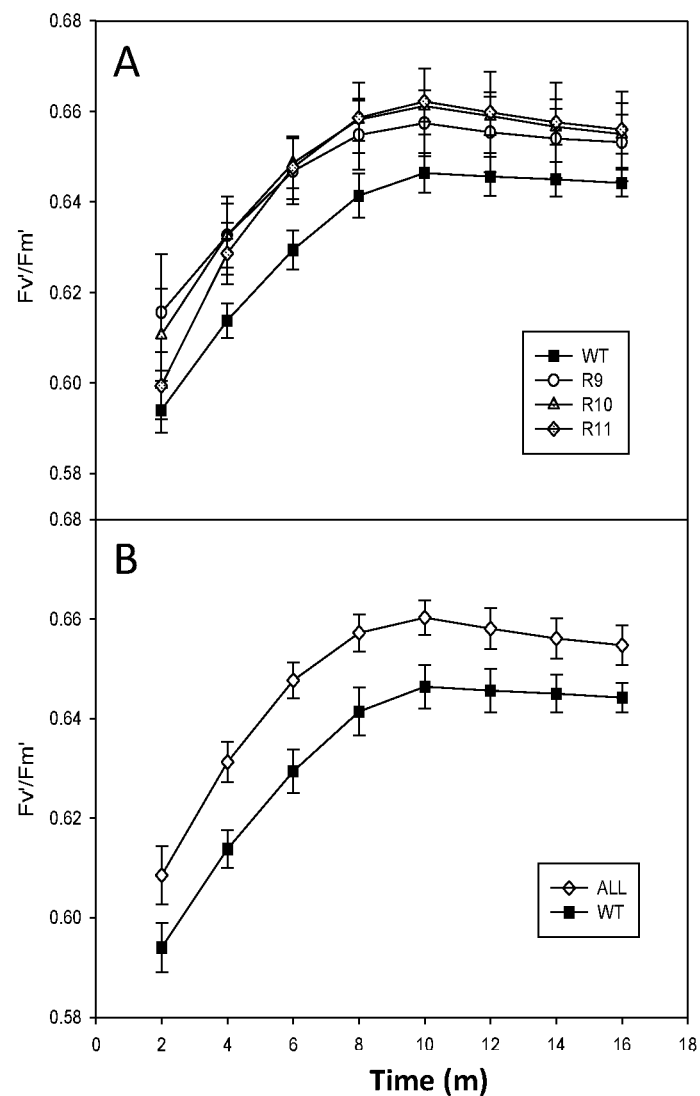

FIG. 17: maximum potential operating efficiency of PSII in the light ($F_v'/F_m'$). (a) $F_v'/F_m'$ for each individual rieskeFeS and (b) all lines combined compared to wild type (WT).

Figure 18:
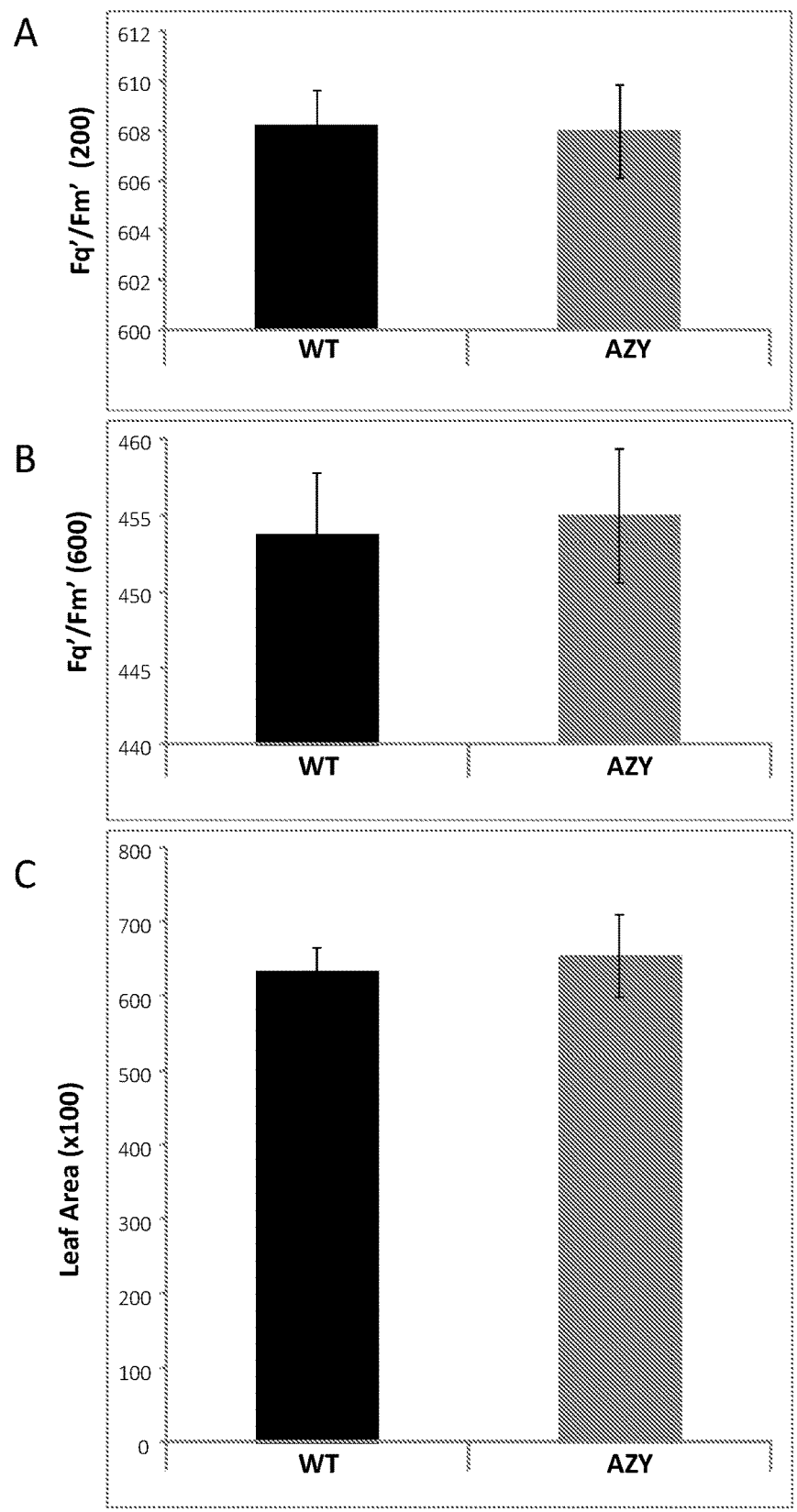

FIG. 18: Comparative analysis of Wild type and null segregants used in this study. WT—wild type plants grown from seed batch. AZY—null segregants recovered from segregating lines verified by PCR for non-integration of the transgene. (a) $F_q'/F_m'$ at 200, (b) $F_q'/F_m'$ at 600, (c) leaf area at the time of analysis.

EXAMPLES

Materials and Methods

Rieske Iron Sulphur Protein of the Cytochrome b6f (Cyt b6f)

The full-length coding sequence of the Rieske iron sulphur protein of the cytochrome b6f (Cyt b6f: X64353) was amplified by RT-PCR using primers NtRieskeFeSF (5'cacc ATGGCTTCTTCTACTCTTTCTCCAG'3 (SEQ ID. No. 4) and NtRieskeFeSR (5' CTAAGCCCACCATGGATCTTCACC'3 (SEQ ID. No. 5). The resulting amplified product was cloned into pENTR/D (Invitrogen, UK) to make pENTR-NtRieskeFeS and the sequence was verified and found to be identical. The full-length cDNA was introduced into the pGWB2 gateway vector (Nakagawa et al., 2007: AB289765) by recombination from the pENTR/D vector to make pGW-NtRieske (B2-NtRi). cDNA are under transcriptional control of the 35s *tobacco mosaic virus* promoter, which directs constitutive high-level transcription of the transgene, and followed by the nos 3' terminator. Construct maps are shown in FIG. 9.

Generation of Transgenic Plants

The recombinant plasmid B2-NtRi was introduced into wild type *Arabidopsis* by floral dipping (Clough and Bent, 1998) using *Agrobacterium tumefaciens* GV3101. Positive transformants were regenerated on MS medium containing kanamycin (50 mg L$^{-1}$), hygromycin (20 mg L$^{-1}$). Kanamycin/hygromycin resistant primary transformants (T1 generation) with established root systems were transferred to soil and allowed to self fertilize.

Plant Growth Conditions

Wild-type T2 *Arabidopsis* plants resulting from self-fertilization of transgenic plants were germinated in sterile agar medium containing Murashige and Skoog salts (plus kanamycin 100 mg for the transformants) and grown to seed in soil (Levington F2, Fisons, Ipswich, UK) and lines of interest were identified by western blot and qPCR. For experimental study, T3 progeny seeds from selected lines were germinated on soil in controlled environment chambers at an irradiance of 130 μmol photons m$^{-2}$ s$^{-1}$, 22° C., relative humidity of 60%, in an 8 h/16 h square-wave photoperiod. Plants were sown randomly and trays rotated daily under the light. Leaf areas were calculated using standard photography and ImageJ software (imagej.nih.gov/ij).

Wild type plants used in this study were a combined group of WT and null segregants from the transgenic lines verified by PCR for non-integration of the transgene. No significant differences in growth parameters were seen between these groups (see FIG. 18).

Protein Extraction and Western Blotting

Four leaf discs (0.6-cm diameter) from two individual leaves, for western blot, were taken and immediately plunged into liquid $N^2$, and stored at −80° C. Samples were ground in liquid nitrogen and protein quantification determined (Harrison et al., 1998). Samples were loaded on an equal protein basis, separated using 12% (w/v) SDS-PAGE, transferred to polyvinylidene difluoride membrane, and probed using antibodies raised against the cytochrome b6 complex proteins PetA (AS08306), PetB (AS03034), and PetC (RieskeFeS: AS08330), PsbA (AS01016), PsaA (AS06172), Lhca1 (AS01005) and against the Glycine decarboxylase H-subunit (AS05074), all purchased from Newmarket Scientific (UK). FBPA antibodies were raised against a peptide from a conserved region of the protein [C]-ASIGLENTEANRQAYR-amide, Cambridge Research Biochemicals, Cleveland, UK (Simkin et al. 2015). Proteins were detected using horseradish peroxidase conjugated to the secondary antibody and ECL chemiluminescence detection reagent (Amersham, Buckinghamshire, UK). Proteins were quantified using a Fusion FX Vilber Lourmat Imager (Peqlab, Lutterworth, UK).

Chlorophyll Fluorescence Imaging

Chlorophyll fluorescence measurements were performed on 10-day-old *Arabidopsis* seedlings that had been grown in a controlled environment chamber providing 130 µmol $mol^{-2}s^{-1}$ photosynthetic photon flux density (PPFD) and ambient $CO_2$ at 22° C. Chlorophyll fluorescence parameters were obtained using a chlorophyll fluorescence (CF) imaging system (Technologica, Colchester, UK; Barbagallo et al., 2003; Baker and Rosenqvist, 2004). The operating efficiency of photosystem two (PSII) photochemistry, $F_q'/F_m'$, was calculated from measurements of steady state fluorescence in the light (F') and maximum fluorescence in the light ($F_m'$) was obtained after a saturating 800 ms pulse of 6200 µmol $m^{-2}$ $s^{-1}$ PPFD using the following equation $F_q'/F_m'=(F_m'-F')/F_m'$. Images of $F_q/F_m$ were taken under stable PPFD of 310, 450 and 600 µmol $m^{-2}$ $s^{-1}$ PPFD (Baker et al., 2001; Oxborough and Baker, 1997).

A/$C_i$ Response Curves

The response of net photosynthesis (A) to intracellular $CO_2$ ($C_i$) was measured using a portable gas exchange system (CIRAS-1, PP Systems Ltd, Ayrshire, UK). Leaves were illuminated using a red-blue light source attached to the gas-exchange system, and light levels were maintained at saturating photosynthetic photon flux density (PPFD) of 1000 µmol $m^{-2}$ $s^{-1}$ with an integral LED light source (PP Systems Ltd, Ayrshire, UK) for the duration of the A/$C_i$ response curve. Measurements of A were made at ambient $CO_2$ concentration ($C_a$) of 400 µmol $mol^{-1}$, before $C_a$ was decreased in a stepwise manner to 300, 200, 150, 100, 50 µmol $mol^{-1}$ before returning to the initial value and increased to 500, 600, 700, 800, 900, 1000, 1100, 1200 µmol $mol^{-1}$. Leaf temperature and vapour pressure deficit (VPD) were maintained at 22° C. and 1±0.2 kPa respectively. The maximum rates of Rubisco—(Vc$_{max}$) and the maximum rate of electron transport for RuBP regeneration (J$_{max}$) were determined and standardized to a leaf temperature of 25° C. based on equations from Bernacchi et al. (2001), and McMurtrie & Wang (1993) respectively.

Photosynthetic Capacity

Photosynthesis as a function of PPFD (A/Q response curves) was measured using a Li-Cor 6400XT portable gas exchange system (Li-Cor, Lincoln, Nebr., USA). Cuvette conditions were maintained at a leaf temperature of 22° C., relative humidity of 50-60%, and ambient growth $CO_2$ concentration (400 mmol $mol^{-1}$ for plants grown in ambient conditions). Leaves were initially stabilized at saturating irradiance 1000 µmol $m^{-2}$ $s^{-1}$, after which A and $g_s$ was measured at the following PPFD levels; 0, 50, 100, 150, 200, 250, 300, 350, 400, 500, 600, 800, 1000 µmol $m^{-2}$ $s^{-1}$. Measurements were recorded after A reached a new steady state (1-2 min) and before stomatal conductance ($g_s$) changed to the new light levels. A/Q analyses were performed at 21% and 2% $O_2$.

Gas Exchange Measurements

The response of net photosynthesis (A) to intracellular $CO_2$ ($C_i$) was measured using a portable gas exchange system (cirus 1). The gas exchange system was zeroed daily using silica gel to remove water and soda lime (sofnolime, Morgan Medical, Kent, UK) to remove $CO_2$ from the air entering the cuvette. Leaves were illuminated using a red-blue light source attached to the gas-exchange system, and light levels were maintained at saturating photosynthetic photon flux density (PPFD) of 1000 µmol $m^{-2}$ $s^{-1}$ with an integral LED light source (PP systems) for the duration of the A/Ci response curve. Measurements of A were made at ambient $CO_2$ concentration ($C_a$) at 400 µmol $mol^{-1}$, before $C_a$ was decreased to 300, 200, 150, 100, 50 µmol $mol^{-1}$ before returning to the initial value and increased to 500, 600, 700, 800, 900, 1000, 1100, 1200 µmol $mol^{-1}$. Leaf temperature and vapour pressure deficit (VPD) were maintained at 22° C. and 1±0.2 kPa respectively. The maximum rates of Rubisco—(Vc$_{max}$) and the maximum rate of electron transport for RuBP regeneration (J$_{max}$) were determined and standardized to a leaf temperature of 25° C. based on equations from Bernacchi et al. (2001), and McMurtrie & Wang (1993), respectively.

PSI and PSII Quantum Efficiency

The photochemical quantum efficiency of PSII and PSI in transgenic and WT plants was measured following a dark-light induction transition using a Dual-PAM-100 instrument (Walz, Effeltrich, Germany) with a DUAL-DR measuring head. Plants were dark adapted for 20 min before placing in the instrument. Following a dark adapted measurement, plants were illuminated with 220 µmol $m^{-2}$ $s^{-1}$ PPFD. The maximum quantum yield of PSII was measured following a saturating pulse of light for 600 ms saturating pulse of light at an intensity of 6200 µmol $m^{-2}$ $s^{-1}$. The PSII operating efficiency was determined as described by the routines above. PSI quantum efficiency was measured as an absorption change of P700 before and after a saturating pulse of 6200 µmol $m^{-2}$ $s^{-1}$ for 300 ms (which fully oxidizes P700) in the presence of far-red light with a FR pre-illumination of 10 s. Both measurements were recorded every minute for 5 min). q$_p$ or ($F_v'/F_m'$), was calculated from measurements of steady state fluorescence in the light (F') and maximum fluorescence in the light ($F_m'$) whilst minimal fluorescence in the light ($F_o'$) was calculated following the equation of Oxborough and Baker (1997b). The fraction of open PSII centres (q$_L$) was calculated from q$_p$×F$_o'$/F (Baker 2008).

Pigment Extraction and HPLC Analysis

Chlorophylls and carotenoids were extracted using n,n-dimethylformamide (DMF) (Inskeep and Bloom 1985) which was subsequently shown to suppressed chlorophyllide formation in *Arabidopsis* leaves (Hu et al., 2013). Briefly, leaf discs collected from two different leaves were immersed in DMF at 4° C. for 48 hours and separated by UPLC as described by Zapata et al., (2000).

Determination of Sucrose and Starch

Carbohydrates and starch were extracted from 20 mg leaf tissue and samples were collected at 2 time points, 1 hour before dawn (15 h into the dark period) and 1 hour before sunset (7 h into the light period). Four leaf discs collected from two different leaves were ground in liquid nitrogen and 20 mg/FW of tissue was incubated in 80% (v/v) ethanol for 20 min at 80° C. and then repeated 3 times with ethanol 80% (v/v) at 80° C. The solid pellet and pooled ethanol samples and freeze dried. Sugars were measured from the extracts in ethanol using an enzyme-based protocol (Stitt et al., 1989), and the starch contents were estimated from the ethanol-insoluble pellet according to Stitt et al. (1978), with the exception that the samples were boiled for 1 h and not autoclaved.

Statistical Analysis

All statistical analyses were done by comparing ANOVA, using Sys-stat, University of Essex, UK. The differences between means were tested using the Post hoc Tukey test (SPSS, Chicago).

Results

Production and Selection of *Arabidopsis* Transformants

The full-length tobacco Rieske iron sulphur coding sequence of the cytochrome b6f complex (Cyt b6f: X64353) was used to generate an over-expression construct B2-NtRi (FIG. 9). Following floral dipping, *Arabidopsis* plants were regenerated on kanamycin/hygromycin containing medium and plants expressing the integrated transgenes were screened using RT-PCR (data not shown).

Total extractable protein from leaves of the T1 progeny was analysed and three lines identified showing a significant over-expression of the RieskeFeS protein (PetC) (FIG. 10A). Immunoblot analysis of T3 progeny from selected lines for *Arabidopsis* expressing RieskeFeS carried out using WT as controls. Immunoblot analysis revealed that all three plants lines selected in the T1 generation showed an accumulation of the RieskeFeS protein (FIG. 1A). Interestingly, the over-expression of RieskeFeS (referred to as Rieske FeS ox) resulted in a concomitant increase in cyt f (PetA) and cyt $b_6$ (PetB), two proteins found within the cytochrome b6f complex (FIG. 1A).

An increase in the level of the PSI type I chlorophyll a/b-binding protein (Lhcal) and an increase in the core protein of PSI (PsaA) was also observed. Furthermore, the DI (PsbA) and D2 (PsbD) proteins which form the reaction centre of PSII were shown to be elevated in Rieske FeS ox lines. Finally, an increase in the ATP synthase delta subunit (AtpD) was also observed in Rieske FeS ox lines (FIG. 1A). As a control for protein loading and expression level (FIG. 1A), the samples were probed with antibodies to the plastidial Calvin-Benson Cycle enzyme FBP aldolase (FBPA) and the mitochondrial photo-respiration enzyme glycine decarboxylase H-subunit (GDCH). No significant differences in protein levels for either FBPA or GDCH were observed. Furthermore, no significant differences in the levels of Rubisco were observed between transgenic and WT plants (FIG. 1A). A quantitative estimate of the changes in protein levels was determined from the immunoblots of samples collected from two to three independent plants per lines. An example is shown in FIG. 1B. These results showed a 2-2.5 fold increase in the Rieske FeS protein relative to WT plants and a similar increase was also observed for cyt f, cyt $b_6$, Lhca1, D2 and PsaA (FIG. 1C). No increase in the stromal FBPA protein was evident.

Chlorophyll Fluorescence Imaging Reveals Increased Photosynthetic Efficiency in Young Transgenic Seedlings In order to screen for photosynthetic changes in seedlings (T3 progeny) grown at either 130 µmol m$^{-2}$ s$^{-1}$ chlorophyll a fluorescence imaging was used to examine the quantum efficiency of PSII photochemistry ($F_q'/F_m'$) (Baker, 2008; Murchie and Lawson, 2013). Analysis of plants over-expressing the cytochrome b6f complex grown at 130 µmol m$^{-2}$ s$^{-1}$, showed a small increase in $F_q'/F_m'$ at an irradiance of 310 µmol m$^{-2}$ s$^{-1}$ (FIG. 2a) and 450 µmol m$^{-2}$ s$^{-1}$ (FIG. 2b) when compared to WT. At higher light level (600 µmol m$^{-2}$s$^{-1}$), significant increase in $F_q'/F_m'$ were still observed (FIG. 11a). Furthermore, no significant differences in Fv/Fm were observed between transgenic and WT (FIG. 11b). From images taken at the time of fluorescence analysis of the seedlings it was shown that the leaf area for all transgenic lines was significantly larger than WT (FIG. 2d). Wild type plants used in this study were a combined group of WT and null segregants verified by PCR. Interestingly, line 11, which showed the largest increase in $F_q'/F_m'$, also showed the biggest increase in leaf area in all experiments. Furthermore, a more detailed analysis of photosynthetic parameters by fluorescence imaging demonstrated a consistent increase in the operating efficiency of PSII ($F_q'/F_m'$; FIG. 15), a decrease in non-photochemical quenching (NPQ; FIG. 2c; FIG. 16) and a significant increase in the maximum potential operating efficiency of PSII in the light ($F_v'/F_m'$; FIG. 17). Wild-type plants used in this study were a combined group of WT and null segregants from the rieskeFeS over-expressing lines verified by PCR. A comparison of wild type plants and null-segregants clearly showed that no significant differences were observed in either photosynthetic efficiency ($F_q'/F_m'$) or in leaf area between the two groups (FIG. 18).

Evaluation of the Relationship Between Carbon Assimilation and Fluorescence at 21% $O_2$ Light response curves conducted to assess the relationship between the photosynthetic operating efficiency ($F_q'/F_m'$) and $CO_2$ fixation corrected for leaf fractional light absorbance ($\phi CO_2$). This provides a measure of the efficiency of light utilization for $CO_2$ fixation. FIG. 3 shows the light response curves carried for each lines independently (FIG. 3a) and all lines combined (FIG. 3b) compared to wild type. The relationship between the photosynthetic operating efficiency and yield of $CO_2$ assimilation enables an assessment of possible alternative electron sinks to Rubisco activity.

Both the operating efficiency of PSII ($F_q'/F_m'$ $\phi CO_2$) (FIG. 3c) and the maximum quantum efficiency of $CO_2$ fixation ($\phi CO_2$) (FIG. 3d) were shown to be elevated compared to wild type when analysed at 21% $O_2$. However, these differences were only significant in line 11 and when all lines were combined into a single group (ALL). Additionally, no significant differences in average stomatal conductance were observed in transgenic lines compared to wild type (FIG. 3e).

Evaluation of the Relationship Between Carbon Assimilation and Fluorescence at 2% $O_2$ In addition to light response curves evaluated at 21% $O_2$, non-photorespiratory conditions (20 mmol mol$^{-1}$ $O_2$) were used for the light response curves to further assess the relationship between the photosynthetic operating efficiency ($F_q'/F_m'$) and $CO_2$ fixation corrected for leaf fractional light absorbance ($\phi CO_2$). This provides a measure of the efficiency of light utilization for $CO_2$ fixation.

FIG. 4 shows the light response curves carried out under non-photorespiratory conditions for each lines independently (FIG. 4a) and all lines combined (FIG. 4c) compared to wild type. The rate of electron transport (rETR) for each line independently compared to wild type is also shown (FIG. 4b). The rETR was shown to be increased in comparison to wild type. The relationship between the photosynthetic operating efficiency and yield of $CO_2$ assimilation enables an assessment of possible alternative electron sinks to Rubisco activity. Both the operating efficiency of PSII ($F_q'/F_m'$ $\phi CO_2$) (FIG. 4d) and the maximum quantum efficiency of $CO_2$ fixation ($\phi CO_2$) (FIG. 4e) were shown to be significantly elevated compared to wild type. Additionally, only minor differences in stomatal conductance were observed in one of the transgenic lines (11) compared to wild type (FIG. 4f).

Increased Quantum Efficiency of PSI and PSII in Comparison to Wild Type

To further explore the influence of increases in the Rieske FeS protein on PSII and PSI photochemistry dark-light induction responses were determined in WT and Rieske FeS ox transgenic plants using simultaneous measurements of P700 oxidation state and PSII efficiency.

FIG. 5 shows that the quantum efficiency of both PSI and PSII were increased in the Rieske FeS ox plants compared to wild type and that the fraction of PSII centres that were open ($q_L$) was also increased whilst the level of Qa reduction (1-qP) was lower in leaves of 27 day old plants. NPQ level was also lower in the Rieske FeS ox plants relative to wild type (FIG. 5A). Furthermore, a reduction in stress induced limitation of NPQ ($q_N$) was also observed.

Increased Cytochrome b6f Protein Levels Stimulates Growth in Low Light

The same group of plants used for fluorescence analysis described above were assembled and photographed (FIG. 7C). Their growth rate was determined by evaluating leaf area over 26 days from planting until such a time that aerial observation became complex due to overlapping leaf areas obscuring evaluated differences. From image analysis of the seedlings it was shown that the leaf area for all lines was significantly greater than WT as early as 3 days after planting onto soil (FIGS. 7A and D). By 16 days, plants over-expressing the Rieske FeS protein were shown to be between 40-114% larger than corresponding wild type plants. Furthermore, line 11 was shown to be significant larger than lines 9 and 10. After 25 days post-planting the plants were destructively harvested and dry weight were determined. Lines 9 to 11 respectively showed a 29%, 46% and 72% increase in biomass compared to WT.

Photosynthetic $CO_2$ Assimilation Rates are Increased in Mature Plants.

The rate of $CO_2$ assimilation (A) was determined in plants grown at 130 µmol $m^{-2}s^{-1}$ as a function of internal $CO_2$ concentration ($C_i$) in young expanding leaves. Under these experimental growth conditions, as previously used for light response curves, no significant differences in $CO_2$ assimilation, $J_{max}$ or $Vc_{max}$ were observed (data not shown). A second group of plants growing at 280 µmol $m^{-2}s^{-1}$ in the green house maintained in square wave light under isolights with a 12 h/12 h day night cycle were also examined (FIG. 6). Under these higher light conditions, in all transgenic plants the rate of A in developing leaves was greater at $C_i$ concentrations above ca. 300 µmol $mol^{-1}$ when compared to WT plants (FIG. 6A-B) resulting in a greater light saturated rate of photosynthesis ($A_{sat}$) in lines 9 and 11 compared with the WT control (FIG. 6C). $A_{sat}$ was clearly elevated in lines ALL compared to WT. Further analysis of the $A/C_i$ curves illustrated that significant enhancements of the maximum rate of Rubisco carboxylation ($Vc_{max}$: FIG. 6D) and electron transport ($J_{max}$: FIG. 6E) were evident in some lines and significantly elevated in ALL. Further analysis of the $A/C_i$ curves illustrated that the light- and $CO_2$-saturated rate of photosynthesis ($A_{max}$) was also significantly greater in 2 of the 3 transgenic lines (FIG. 6C). An analysis of final leaf area and final dry eight (biomass) of the plants used here showed an overall significant increase in both leaf area (FIG. 7A) and final biomass (FIG. 7B)

Increased cytochrome b6f protein levels stimulates growth in low light. The same group of plants used for fluorescence analysis described above were assembled and photographed (FIG. 8A). Their growth rate was determined by evaluating rosette area over 26 days from planting until such a time that aerial observation became complex due to overlapping leaf areas obscuring evaluated differences. From image analysis of the seedlings it was shown that the leaf area for all lines was significantly greater than WT as early as 8 days after planting onto soil (FIG. 8B). By 16 days, plants over-expressing the RieskeFeS protein were shown to be between 40-114% larger than corresponding wild type plants. Furthermore, line 11 was shown to be significant larger than lines 9 and 10.

After 25 days post-planting the plants were destructively harvested and dry weight were determined. Lines 9 to 11 respectively showed a 29%, 46% and 72% increase in biomass compared to WT (FIG. 8C).

Over-Expression of the RieskeFeS Protein Results in Changes to the Pigment Content of Transgenic Lines.

Four leaf discs from two different leaves from selected lines were collected and the pigments were extracted using DMF and pigments were separated by UPLC as described by Zapata et al., (2000). An average 26% increase in chlorophyll content was observed in transgenic lines. These increases were accompanied by an increase in neoxanthin (+38%), violaxanthin (+59%), lutein (+75%) and β-carotene (+169%). Chlorophyll ratios of approx 3.05-3.10 in both WT and transgenic lines is similar to the 3.11 previously reported in coffee leaves and 2.94 in green coffee cherries (Simkin et al., 2008; 2010). Interestingly, line 11 (previously shown to have an overall higher increase in PSII efficiency (FIG. 2), higher average increases in $A_{max}$ (FIGS. 3, 4 and 6) and a faster growth rate (FIG. 8) was shown to have the highest increase in both chlorophyll and carotenoids compared to WT (see Table 1).

TABLE 1 shows pigment content in WT and transgenic lines. Results are represented as units of β-carotene in WT (where β-carotene in WT = 1).

|  | WT | 9 | 10 | 11 | ALL |
|---|---|---|---|---|---|
| Neoxanthin | 0.90 +/− 0.08 | 1.22 +/− 0.08* | 1.17 +/− 0.08* | 1.33 +/− 0.10** | 1.24 +/− 0.05** |
| Violaxanthin | 0.92 +/− 0.08 | 1.42 +/− 0.08*** | 1.39 +/− 0.10*** | 1.58 +/− 0.10*** | 1.46 +/− 0.05*** |
|  | Violaxanthin | +54% | +51% | +71% | +55% |
| Lutein | 3.09 +/− 0.25 | 5.36 +/− 0.40*** | 5.05 +/− 0.31*** | 5.84 +/− 0.28*** | 5.42 +/− 0.20*** |
|  | Lutein | +73% | +63% | +89% | +75% |
| β-carotene | 1.00 +/− 0.10 | 2.71 +/− 0.19*** | 2.45 +/− 0.18*** | 2.92 +/− 0.08*** | 2.69 +/− 0.10*** |
|  | β-carotene | +171% | +145% | +192% | +169% |

TABLE 1-continued shows pigment content in WT and transgenic lines. Results are represented as units of β-carotene in WT (where β-carotene in WT = 1).

|  | WT | 9 | 10 | 11 | ALL |
|---|---|---|---|---|---|
| total car | 5.91 +/− 0.44 | 10.06 +/− 0.64* | 10.71 +/− 0.55* | 11.67 +/− 0.42* | 10.81 +/− 0.35* |
| chl/a | 15.56 +/− 0.50 | 19.82 +/− 1.01* | 18.31 +/− 0.95 | 20.83 +/− 0.79* | 19.65 +/− 0.56* |
| chl/b | 5.11 +/− 0.17 | 6.41 +/− 0.27 | 5.87 +/− 0.27* | 6.73 +/− 0.32* | 6.34 +/− 0.18* |
| chl total | 20.67 +/− 0.61 chlorophyll | 26.23 +/− 1.26* +27% | 24.18 +/− 1.21 +17% | 27.55 +/− 1.10* +33% | 27.55 +/− 1.10* +26% |
| ratio chl a/b | 3.05 | 3.09 | 3.12 | 3.10 | 3.10 |
| chl/βC | 20.67 | 9.68 | 9.87 | 9.43 | 9.65 |
| chl/Lutien | 6.68 | 4.89 | 4.79 | 4.72 | 4.8 |

Statistical differences are shown in bold (*<0.1; <0.05; *<0.001).

Discussion

The primary determinant of plant productivity is associated directly with photosynthetic efficiency and any improvements, through genetic manipulation or otherwise, can greatly influence biomass and yield.

Certain embodiments of the present invention illustrate that increasing the level of the RieskeFeS protein component of the cyt 6bf complex results in a co-committant increase in other components of the complex, PetA and PetB. Certain embodiments of the present invention may also result in a co-committant increase in the PSI type I chlorophyll a/b-binding protein (Lhcal) and the core protein of PSI (PsaA) and PsbA, PsbD of the PSII reaction centre and the ATP synthase delta subunit (AtpD). The combined increase of the cyt b6f complex and other identified proteins results in a substantial and significant impact on photosynthesis and biomass of *Arabidopsis* grown under standard growth room conditions.

Chlorophyll fluorescence imaging used to analyse plants at 14 days post-planting demonstrated that the positive effect of the manipulation on the cyt b6f complex is evident at an early stage of development. Interestingly, lines 11, which showed the largest overall increases in photosynthetic efficiency ($F_q'/F_m'$ and $A_{max}$) also showed the largest increase in leaf area and biomass when compared to WT.

CONCLUSION

As demonstrated herein, over-expression of RieskeFeS protein, a key component of the cytobrome b6f complex, resulted in a co-commitant increase in the protein levels of several other components of the complex as well as other proteins involved electron transport and plant growth.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

Anderson, J. M. (1992). Cytochrome b6f complex: dynamic molecular organization, function and acclimation. *Photosynth. Res.* 34, 341-357.doi:10.1007/BF00029810

Anderson, J. M., Price, G. D., Chow, W. S., Hope, A. B., and Badger, M. R. (1997). Reduced levels of cytochrome bf complex in transgenic tobacco leads to marked photochemical reduction of the plastoquinone pool, without significant change in acclimation to irradiance. *Photosynth. Res.* 53, 215-227.doi: 10.1023/A:1005856615915

Baker N R (2008). Chlorophyll fluorescence: a probe of photosynthesis in vivo. 2008. *Annual Review of Plant Biology* 59, 89-113.

Baker N R, Oxborough K, Lawson T, Morison J I (2001) High resolution imaging of photosynthetic activities of tissues, cells and chloroplasts in leaves. *Journal of Experimental Botany* 52: 615-621

Baker N R, Rosenqvist E (2004) Applications of chlorophyll fluorescence can improve crop production strategies: an examination of future possibilities. *Journal of Experimental Botany* 55, 1607-1621.

Barbagallo R P, Oxborough K, Pallett K E, Baker N R (2003) Rapid, non-invasive screening for perturbations of metabolism and plant growth using chlorophyll fluorescence imaging. *Plant Physiology* 132, 485-493.

Bernacchi C. J., Singsaas E. L., Pimentel C., Portis Jr A. R. & Long S. P. (2001) Improved temperature response functions for models of Rubisco-limited photosynthesis. *Plant, Cell and Environment* 24, 253-260.

Clough S J, Bent A F. 1998. Floral dip: a simplified method for *Agrobacterium*-mediated transformation of *Arabidopsis thaliana*. *Plant Journal* 16, 735-743.

Farquhar G D, von Caemmerer S, Berry J A. 1980. A biochemical model of photosynthetic $CO_2$ assimilation in leaves of C3 species. *Planta* 149, 78-90.

Fischer R A, Edmeades G O. 2010. Breading and crop Yield Progress. Crop Science Society of America 677 S. Segoe Rd., Madison, Wis. 53711 USA 50, S85-S98.

Harrison E P, Willingham N M, Lloyd J C, Raines C A. 1998. Reduced sedoheptulose-1,7-bisphosphatase levels in transgenic tobacco lead to decreased photosynthetic capacity and altered carbohydrate accumulation. *Planta* 204 27-36.

Haehnel, W. (1984). Photosynthetic electron transport in higher plants. *Ann. Rev. Plant Physiol.* 35, 659-693.doi: 10.1146/annurev.pp.35.060184.003303

Hope, A. B. (2000). Electron transfer amongst cytochrome f, plastocyanin, and photosystem I: kinetics and mechanisms. *Biochim. Biophys. Acta* 1456, 5-26.doi: 10.1016/S0005-2728(99)00101-2

Hu X, Tanaka A, Tanaka R. (2013). Simple extraction methods that prevent the artifactual conversion of chlorophyll to chlorophyllide during pigment isolation from leaf samples. Plant Methods. 9: 19

Inskeep W P, Bloom P R. 1985. Extinction coefficients of chlorophyll a and b in n,n-dimethylformamide and 80% acetone. *Plant Physiol* 1985, 77:483-485

Kirchhoff, H., Horstmann, S., and Weis, E. (2000). Control of photosynthetic electron transport by PQ diffusion microdomains in thylakoids of higher plants. *Biochim. Biophys. Acta* 1459, 148-168.doi:10.1016/S0005-2728 (00)00143-2

Lefebvre S, Lawson T, Zakhleniuk O V, Lloyd J C, Raines C A. 2005. Increased sedoheptulose-1,7-bisphosphatase activity in transgenic tobacco plants stimulates photosynthesis and growth from an early stage in development. *Plant Physiol* 138: 451-460

Long S P, Zhu X G, Naidu S L, Ort D R. 2006. Can improvement in photosynthesis increase crop yields? *Plant, Cell & Environment* 29, 315-330.

López-Juez E., Jarvis R. P., Takeuchi A., Page A. M., & Chory J. (1998) New *Arabidopsis* cue mutants suggest a close connection between plastid- and phytochrome regulation of nuclear gene expression. *Plant Physiol* 118, 803-815.

McMurtrie R. E. & Wang Y. P. (1993) Mathematical models of the photosynthetic response of tree stands to rising CO2 concentrations and temperature *Plant, Cell and Environment* 16, 1-13.

Murchie E H, Lawson T. 2013 Chlorophyll fluorescence analysis: guide to good practice and understanding some new applications. *Journal of Experimental Botany.* 64, 3983-3998.

Nakagawa T, Kurose T, Hino T, Tanaka K, Kawamukai M, Niwa Y, Toyooka K, Matsuoka K, Jinbo T, Kimura T. (2007). Development of series of gateway binary vectors, pGWBs, for realizing efficient construction of fusion genes for plant transformation. J. Biosci. Bioeng. 104 (1), 34-41.

Oxborough K, Baker N R. 1997. An instrument capable of imaging chlorophyll a Fluorescence from intact leaves at very low irradiance and at cellular and subcellular levels. *Plant Cell and Environment* 20, 1473-1483.

Oxborough K. & Baker N. R. (1997b). Resolving chlorophyll a fluorescence images of photosynthetic efficiency into photochemical and nonphotochemical components—calculation of qP and Fv/Fm without measuring *Fo. Photosynthesis. Research.* 54, 135-142.

Parry M A J, Reynolds M, Salvucci M E, Raines C, Andralojc P J, Zhu X G, Price G D, Condon A G, Furbank R T. 2011. Raising yield potential of wheat. II. Increasing photosynthetic capacity and efficiency. *Journal of Experimental Botany* 62, 453-467.

Price, G. D., von Caemmerer, S., Evans, J. R., Siebke, K., Anderson, J. M., and Badger, M. R. (1998). Photosynthesis is strongly reduced by antisense suppression of chloroplastic cytochrome bf complex in transgenic tobacco. *Aust. J. Plant Physiol.* 25, 445-452.doi:10.1071/PP97164

Price, G. D., Yu, J. W., von Caemmerer, S., Evans, J. R., Chow, W. S., Anderson, J. M., et al. (1995). Chloroplast cytochrome b6/f and ATP synthase complexes in tobacco: transformation with antisense RNA against nuclear-encoded transcripts for the RieskeFeS and ATP polypeptides. *Aust. J. Plant Physiol.* 22, 285-297.doi: 10.1071/PP9950285

Raines C A. 2011. Increasing photosynthetic carbon assimilation in C3 plants to improve crop yield: current and future strategies. *Plant Physiology* 155, 36-42.

Sharkey T D, Bernacchi C J, Farquhar G D, Singsaas E L. 2007. Fitting photosynthetic carbon dioxide response curves for C-3 leaves. *Plant, Cell & Environment* 30, 1035-1040

Simkin A J, McAusland L, Headland L R, Lawson T, Raines C A (2015) Multigene manipulation of photosynthetic carbon assimilation increases CO2 fixation and biomass yield. *Journal of Experimental Botany.* 66(13):4075-4090.

Stitt M, Bulpin P V, ap Rees T. 1978. Pathway of starch breakdown in photosynthetic tissues of *Pisum sativum. Biochimica et Biophysica Acta* 544, 200-214.

Yamori, W., Takahashi, S., Makino, A., Price, G. D., Badger, M. R., and von Caemmerer, S. (2011). The roles of ATP synthase and the cytochrome b6/f complex in limiting chloroplast electron transport and determining photosynthetic capacity. *Plant Physiology* 155, 956-962. doi: 10.1104/pp.110.168435

Zapata M, Rodríguez F, Garrido J L. 2000. Separation of chlorophylls and carotenoids from marine phytoplankton, a new HPLC method using a reversed phase C8 column and phridine-containing mobile phases. *Mar Ecol Prog Ser,* 195:29-45.

Zhu X G, Long S P, Ort D R. 2010. Improving photosynthetic efficiency for greater yield. *Annual Review of Plant Biology* 61, 235-226.

The invention claimed is:

1. A method of increasing a photosynthesis rate of a plant, the method comprising genetically modifying said plant to overexpress within said plant Rieske iron sulphur protein to form a genetically modified plant with increased photosynthesis, wherein the Rieske iron sulphur protein has at least 70% sequence identity to SEQ ID NO: 1 or a plant PetC protein, wherein the Rieske iron sulphur protein is encoded by a nucleic acid molecule that is operably linked to a promoter operable in a plant cell, and wherein the genetic modification comprises or is to the promoter, the nucleic acid molecule or both.

2. The method according to claim 1, wherein:
(i) the genetically modified plant has an increased photosynthesis rate as compared to a control plant;
(ii) the genetically modified plant has a greater size, greater biomass and/or faster growth rate as compared to a control plant; or (iii) the genetically modified plant has an enhanced yield as compared to a control plant;
wherein the control plant is a wild-type plant of the same variety as the genetically modified plant.

3. The method according to claim 1, wherein the method further comprises:
(i) introducing into at least one plant cell an expression vector comprising the nucleic acid molecule encoding an Rieske iron sulphur protein; and
(ii) regenerating a genetically modified plant from said at least one plant cell.

4. The method according to claim 1, which further comprises cultivating the genetically modified plant under conditions promoting plant growth and development;
(i) obtaining a progeny of said genetically modified plant;
(ii) cultivating the progeny of the genetically modified plant under conditions suitable for photosynthesis to occur; and
(iii) determining an increased photosynthesis rate of the progeny of the genetically modified plant.

5. The method according to claim 1, wherein overexpression of the Rieske iron sulphur protein increases expression of a cytochrome b6f complex protein in at least one plant cell of the genetically modified plant.

6. The method according to claim 5, wherein:
(i) the cytochrome b6f complex protein is selected from PetA, PetB and a combination of PetA and PetB; and/or
(ii) the cytochrome b6f complex protein is an endogenous cytochrome b6f complex protein.

7. A method according to claim 1, wherein the Rieske iron sulphur protein comprises the amino acid sequence as set forth in SEQ. ID. No. 1.

8. The method according to claim 1, wherein the Rieske iron sulphur protein has at least 70% sequence identity to the amino acid set forth in SEQ. ID. No. 1.

9. The method according to claim 3, wherein the nucleic acid molecule comprises a nucleic acid sequence selected from:
a) a nucleic acid sequence as set forth in SEQ. ID. No. 2 or SEQ. ID. No. 3;
b) a nucleic acid sequence having at least 70% sequence identity to the nucleic acid sequence as set forth in SEQ. ID. No. 2 or SEQ. ID. No. 3 and which encodes a Rieske iron sulphur protein;
c) a nucleic acid sequence which hybridises to (a) or (b) and which encodes a Rieske iron sulphur protein; and
d) a nucleic acid sequence which differs from (a), (b) or (c) by virtue of the degeneracy of the genetic code and which encodes a Rieske iron sulphur protein.

10. The method according to claim 3, wherein the nucleic acid molecule is an isolated nucleic acid molecule.

11. The method according to claim 3, wherein the expression vector is a plasmid suitable for nuclear transformation.

12. A chimeric construct for increased expression of a cytochrome b6f protein in a plant, the chimeric construct comprising a nucleic acid molecule, which encodes a Rieske iron sulphur protein, operably linked to a promoter which is operable in a plant cell, wherein the nucleic acid molecule comprises a nucleic acid sequence selected from:
i) a nucleic acid sequence as set forth in SEQ. ID. No. 2 or SEQ. ID. No. 3;
ii) a nucleic acid sequence having at least 70% sequence identity to the nucleic acid sequence as set forth in SEQ. ID. No. 2 or SEQ. ID. No. 3 and which encodes a Rieske iron sulphur protein;
iii) a nucleic acid sequence which hybridises to (a) or (b) and which encodes a Rieske iron sulphur protein; and
iv) a nucleic acid sequence which differs from (a), (b) or (c) by virtue of the degeneracy of the genetic code and which encodes a Rieske iron sulphur protein.

13. A plant cell comprising a nucleic acid molecule comprising an exogenous nucleic acid sequence selected from:
a) a nucleic acid sequence as set forth in SEQ. ID. No. 2 or SEQ. ID. No. 3;
b) a nucleic acid sequence having at least 70% sequence identity to the nucleic acid sequence as set forth in SEQ. ID. No. 2 and which encodes a Rieske iron sulphur protein;
c) a nucleic acid sequence which hybridises to (a) or (b) and which encodes a Rieske iron sulphur protein; and
d) a nucleic acid sequence which differs from (a), (b) or (c) by virtue of the degeneracy of the genetic code, wherein the nucleic acid molecule encodes an Rieske iron sulphur protein.

14. The method of increasing a photosynthesis rate of a genetically modified plant of claim 1, wherein the Rieske iron sulphur protein:
a) has an amino acid sequence having at least 70% sequence identity to the amino acid set forth in SEQ. ID. No. 1;
b) is encoded by a nucleic acid sequence having at least 70% identify sequence identity to the nucleic acid sequence as set forth in SEQ ID. No. 2 or SEQ ID No. 3;
c) is encoded by a nucleic acid sequence which hybridises to (a) or (b); or
d) is encoded by a nucleic acid sequence which differs from (b) or (c) by virtue of the degeneracy of the genetic code.

15. The method of claim 14, wherein the plant is wheat.

16. The plant cell of claim 13, further comprising a promoter operably linked to the nucleic acid molecule.

17. The plant cell of claim 16, wherein the promoter is a 35s tobacco mosaic virus promoter.

* * * * *

SEQUENCE LISTING

```
<160> NUMBER OF SEQ ID NOS: 5

<210> SEQ ID NO 1
<211> LENGTH: 228
<212> TYPE: PRT
<213> ORGANISM: Nicotiana tabacum
<220> FEATURE:
<221> NAME/KEY: MISC_FEATURE
```

<223> OTHER INFORMATION: N. tabacum RieskeFeS protein

<400> SEQUENCE: 1

```
Met Ala Ser Ser Thr Leu Ser Pro Val Thr Gln Leu Cys Ser Ser Lys
1               5                   10                  15

Ser Gly Leu Ser Ser Val Ser Gln Cys Leu Leu Leu Lys Pro Met Lys
            20                  25                  30

Ile Asn Ser His Gly Leu Gly Lys Asp Lys Arg Met Lys Val Lys Cys
        35                  40                  45

Met Ala Thr Ser Ile Pro Ala Asp Asp Arg Val Pro Asp Met Glu Lys
    50                  55                  60

Arg Asn Leu Met Asn Leu Leu Leu Gly Ala Leu Ser Leu Pro Thr
65                  70                  75                  80

Ala Gly Met Leu Val Pro Tyr Ala Thr Phe Phe Ala Pro Pro Gly Ser
                85                  90                  95

Gly Gly Gly Ser Gly Gly Thr Pro Ala Lys Asp Ala Leu Gly Asn Asp
            100                 105                 110

Val Ile Ala Ser Glu Trp Leu Lys Thr His Pro Pro Gly Asn Arg Thr
        115                 120                 125

Leu Thr Gln Gly Leu Lys Gly Asp Pro Thr Tyr Leu Val Val Glu Asn
    130                 135                 140

Asp Gly Thr Leu Ala Thr Tyr Gly Ile Asn Ala Val Cys Thr His Leu
145                 150                 155                 160

Gly Cys Val Val Pro Phe Asn Ala Ala Glu Asn Lys Phe Ile Cys Pro
                165                 170                 175

Cys His Gly Ser Gln Tyr Asn Asn Gln Gly Arg Val Val Arg Gly Pro
            180                 185                 190

Ala Pro Leu Ser Leu Ala Leu His Ala Asp Ile Asp Asp Gly Lys
        195                 200                 205

Val Val Phe Val Pro Trp Val Glu Thr Asp Phe Arg Thr Gly Glu Asp
    210                 215                 220

Pro Trp Trp Ala
225
```

<210> SEQ ID NO 2
<211> LENGTH: 666
<212> TYPE: DNA
<213> ORGANISM: Nicotiana tabacum
<220> FEATURE:
<221> NAME/KEY: misc_feature
<223> OTHER INFORMATION: N. tabacum PetC cDNA

<400> SEQUENCE: 2

```
atggcttctt ctactctttc tccagtaact cagctatgct cgagcaagag tggtttgtct      60
tcagtttcac aatgtttgct actgaagcca atgaagatta acagtcatgg attgggaaag     120
gataagagga tgaaagtcaa gtgcatggct acaagcattc cagcagatga tagagtgcct     180
gatatggaaa agaggaatct catgaatttg cttcttttgg gtgctctttc tctacccact     240
gctgggatgt tggtacctta tgctactttc tttgcaccac ctgggtcagg ggtggtagt     300
ggtggaaccc ctgccaagga tgcattaggt aatgatgtca ttgcatctga atggctcaaa     360
actcatccac ccggcaaccg aactctcacg caaggactaa agggagatcc tacttacctt     420
gttgtggaga atgatggaac acttgcaacc tatggtatta atgctgtgtg tactcaccct     480
ggttgtgttg tgccatttaa tgctgctgag aacaagttta tttgccctg ccatggatct     540
caatataaca accaaggaag agttgttaga ggacctgctc ctttgtcctt ggcattggct     600
```

```
catgctgaca ttgatgatgg aaggtggtg tttgtcccat gggttgaaac agacttcaga    660
actggt                                                              666

<210> SEQ ID NO 3
<211> LENGTH: 833
<212> TYPE: DNA
<213> ORGANISM: Nicotiana tabacum
<220> FEATURE:
<221> NAME/KEY: misc_feature
<223> OTHER INFORMATION: N. tabacum PetC gene

<400> SEQUENCE: 3
aaatggcttc ttctactctt tctccagtaa ctcagctatg ctcaagcaag agtggcttgt    60
cttcagtttc acaatgtttg ctagtgaagc caatgaagat taacagtcat ggattgggaa   120
aagataagag gatgaaagtg aaatgcatgg ctacaagtat tccagcagat gatagagtgc   180
ctgatatgga aaagaggaat ctcatgaatt tgcttctttt gggtgctctt tctctaccca   240
ctgctgggat gttggtatct tatggtactt tctttgtacc acctgggtca gggggtggta   300
gtggtggaac ccctgccaag gatgcattag gtaatgatgt cattgcatct gaatggctca   360
aaactcatcc acctggcaac cgaactctca cgcaaggact aaagggagac cctacttacc   420
ttgttgtgga gaatgatgga acagttgcaa cctatggtat taatgctgtg tgtactcacc   480
ttggttgtgt tgtgccatt aatgctgctg agaacaagtt tatttgcccc tgccatggat   540
ctcaatacaa caaccaagga agagttgtta gaggacctgc tcccttgtcc ttggcattgg   600
ctcatgctga tattgatgat gggaaggtgg tgtttgtccc atgggttgaa acagacttca   660
gaactggtga agatccatgg tgggcttaga tctccttatc actatattat cctcttgtat   720 cttgttaca taagcttat ctccttttta tgaagcaaaa agaaatattc attttgatga    780
tgtaactatt gaaggataac ctttgcagtc ccataatgac attttttgtt taa          833

<210> SEQ ID NO 4
<211> LENGTH: 29
<212> TYPE: DNA
<213> ORGANISM: Artificial Sequence
<220> FEATURE:
<223> OTHER INFORMATION: RT-PCR Primer 1

<400> SEQUENCE: 4
caccatggct tcttctactc tttctccag                                       29

<210> SEQ ID NO 5
<211> LENGTH: 24
<212> TYPE: DNA
<213> ORGANISM: Artificial Sequence
<220> FEATURE:
<223> OTHER INFORMATION: RT-PCR Primer 2

<400> SEQUENCE: 5
ctaagcccac catggatctt cacc                                            24
```